(12) United States Patent
Leveille et al.

(10) Patent No.: US 11,819,219 B2
(45) Date of Patent: Nov. 21, 2023

(54) TIBIA CUTTING ASSEMBLY

(71) Applicant: ORTHOSOFT ULC, Montreal (CA)

(72) Inventors: Catherine Leveille, Montréal (CA); Benoit Pelletier, Montreal (CA); Bruno Falardeau, Verdun (CA); Karine Duval, Montreal (CA)

(73) Assignee: ORTHOSOFT ULC, Montreal (CA)

( * ) Notice: Subject to any disclaimer, the term of this patent is extended or adjusted under 35 U.S.C. 154(b) by 655 days.

(21) Appl. No.: 16/909,302

(22) Filed: Jun. 23, 2020

(65) Prior Publication Data

US 2020/0315635 A1    Oct. 8, 2020

Related U.S. Application Data

(63) Continuation of application No. 16/007,270, filed on Jun. 13, 2018, now Pat. No. 10,729,452.

(60) Provisional application No. 62/518,826, filed on Jun. 13, 2017.

(51) Int. Cl.

| | |
|---|---|
| *A61B 17/15* | (2006.01) |
| *A61B 17/17* | (2006.01) |
| A61B 17/00 | (2006.01) |
| A61B 90/00 | (2016.01) |
| A61B 34/10 | (2016.01) |
| A61B 34/20 | (2016.01) |

(52) U.S. Cl.
CPC ........ *A61B 17/157* (2013.01); *A61B 17/1764* (2013.01); *A61B 34/10* (2016.02); *A61B 2017/00477* (2013.01); *A61B 2034/2048* (2016.02); *A61B 2090/3983* (2016.02)

(58) Field of Classification Search
CPC .............. A61B 17/1764; A61B 17/157; A61B 2034/2048
See application file for complete search history.

(56) References Cited

U.S. PATENT DOCUMENTS

| 8,696,675 | B2 | 4/2014 | Boutin |
| 9,271,756 | B2* | 3/2016 | van der Walt ......... A61B 34/10 |
| 2011/0208093 | A1 | 8/2011 | Gross et al. |
| 2012/0053594 | A1 | 3/2012 | Pelletier et al. |
| 2014/0276000 | A1 | 9/2014 | Mullaney |
| 2019/0254682 | A1 | 8/2019 | Amiot |

FOREIGN PATENT DOCUMENTS

| FR | 3034004 A1 | 9/2016 |
| WO | 2012027815 A1 | 3/2012 |
| WO | 2012027816 A1 | 3/2012 |
| WO | 2017056034 A1 | 4/2017 |

* cited by examiner

*Primary Examiner* — Andrew Yang
(74) *Attorney, Agent, or Firm* — NORTON ROSE FULBRIGHT CANADA LLP

(57) ABSTRACT

A tibia cutting assembly includes a tibia cut guide with at least one cut slot. A guide rod has a guide holder mountable to the cut guide at a first end of the guide rod, and a second end of the guide rod is mountable non-invasively about a skin of a patient. The guide rod is extendable in length to displace the tibia cut guide and adjust a position thereof with respect to a tibia of the patient. The guide holder cooperates with the tibia cut guide to adjust an orientation of the tibia cut guide. A first inertial sensor is mountable to the guide holder and is displaceable therewith, and a second inertial sensor is mountable to the guide rod at the second end thereof.

19 Claims, 13 Drawing Sheets

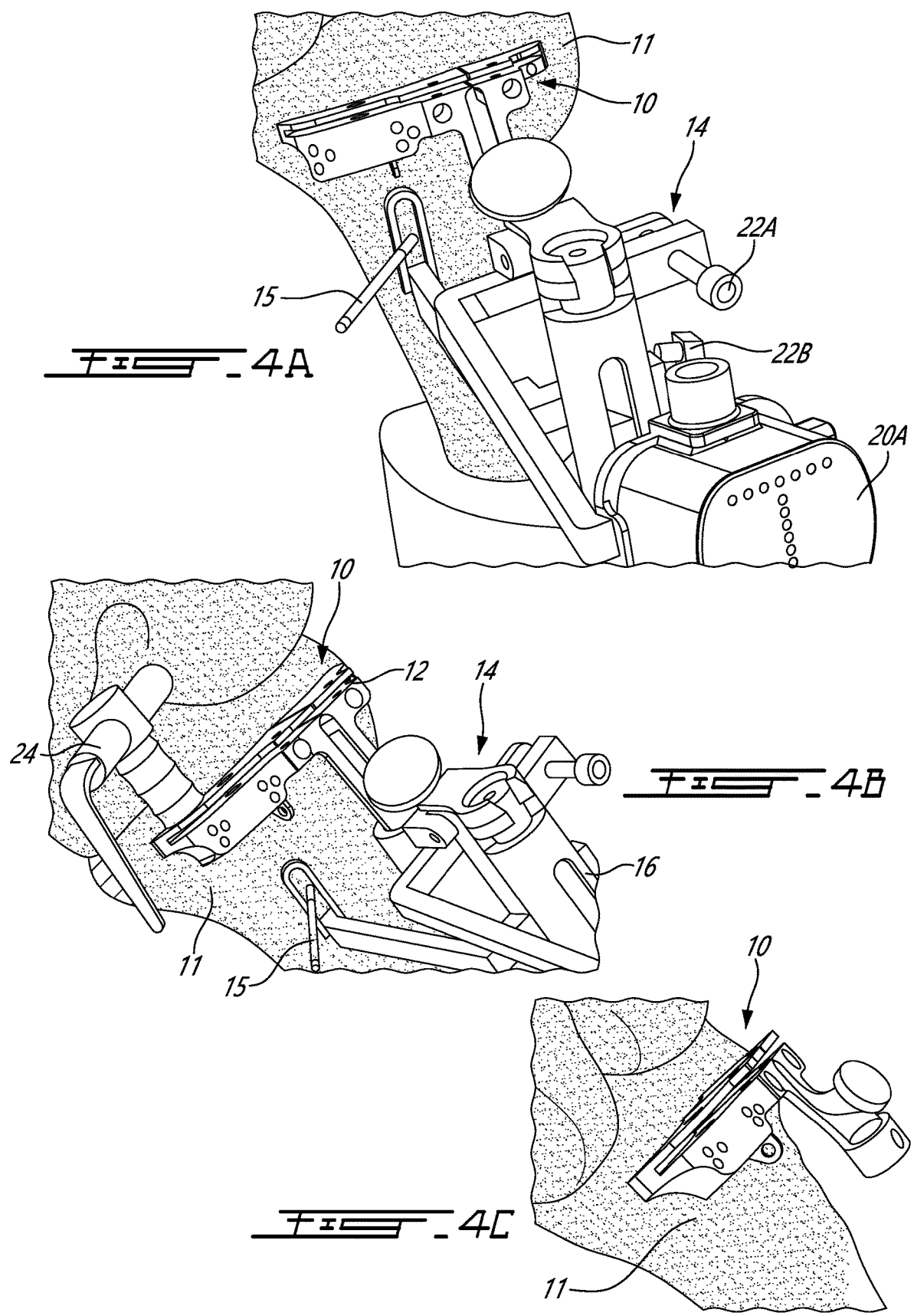

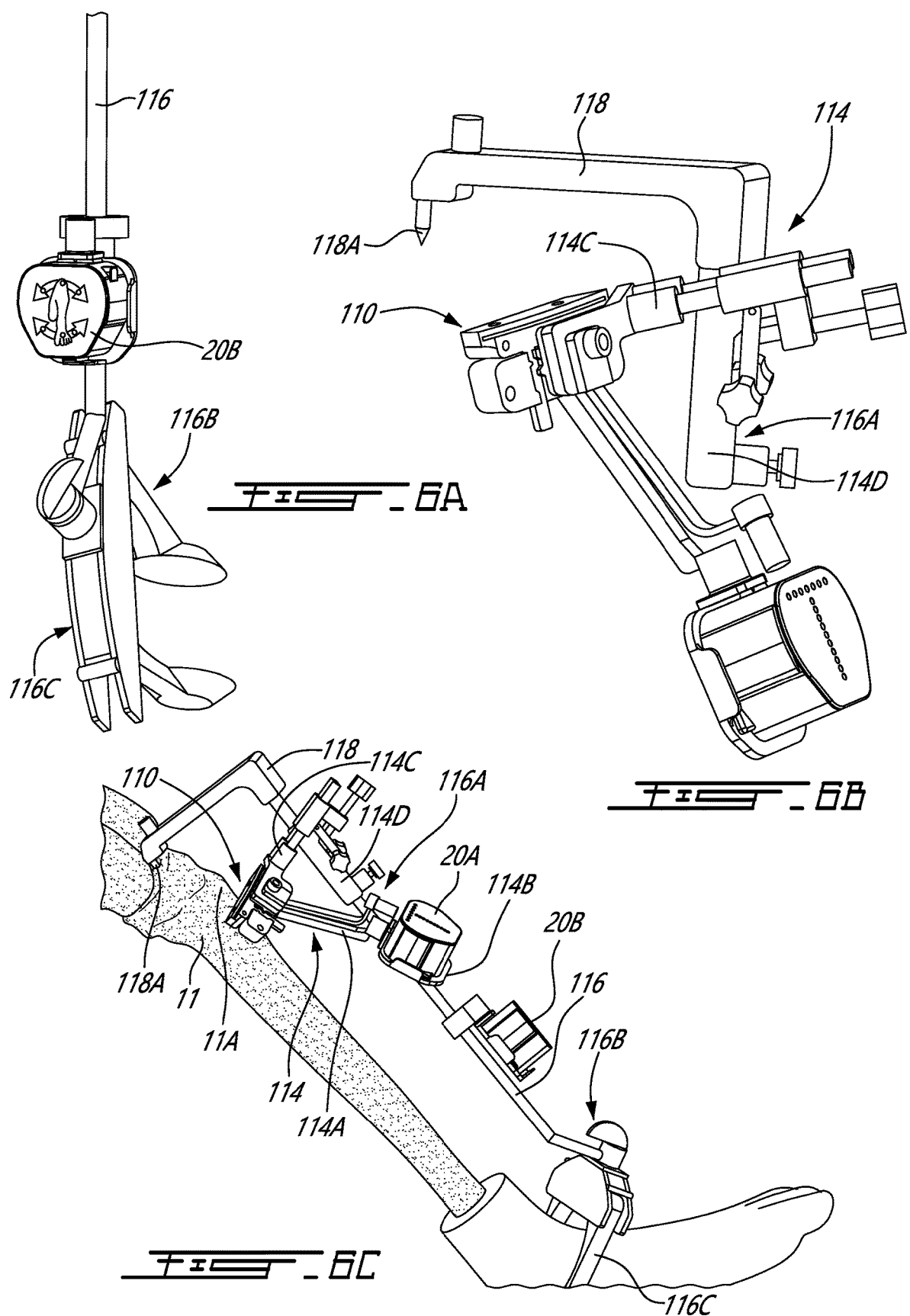

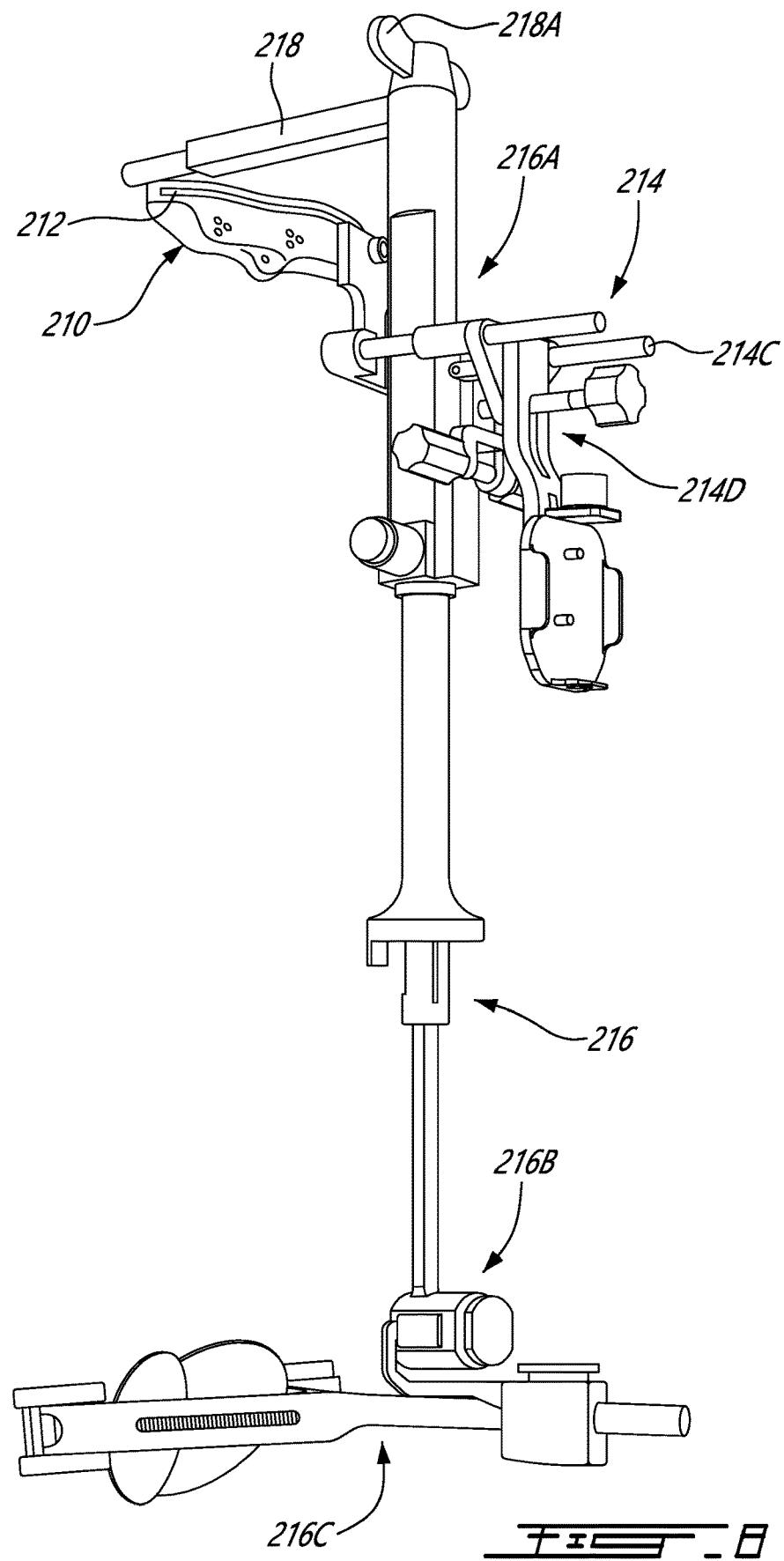

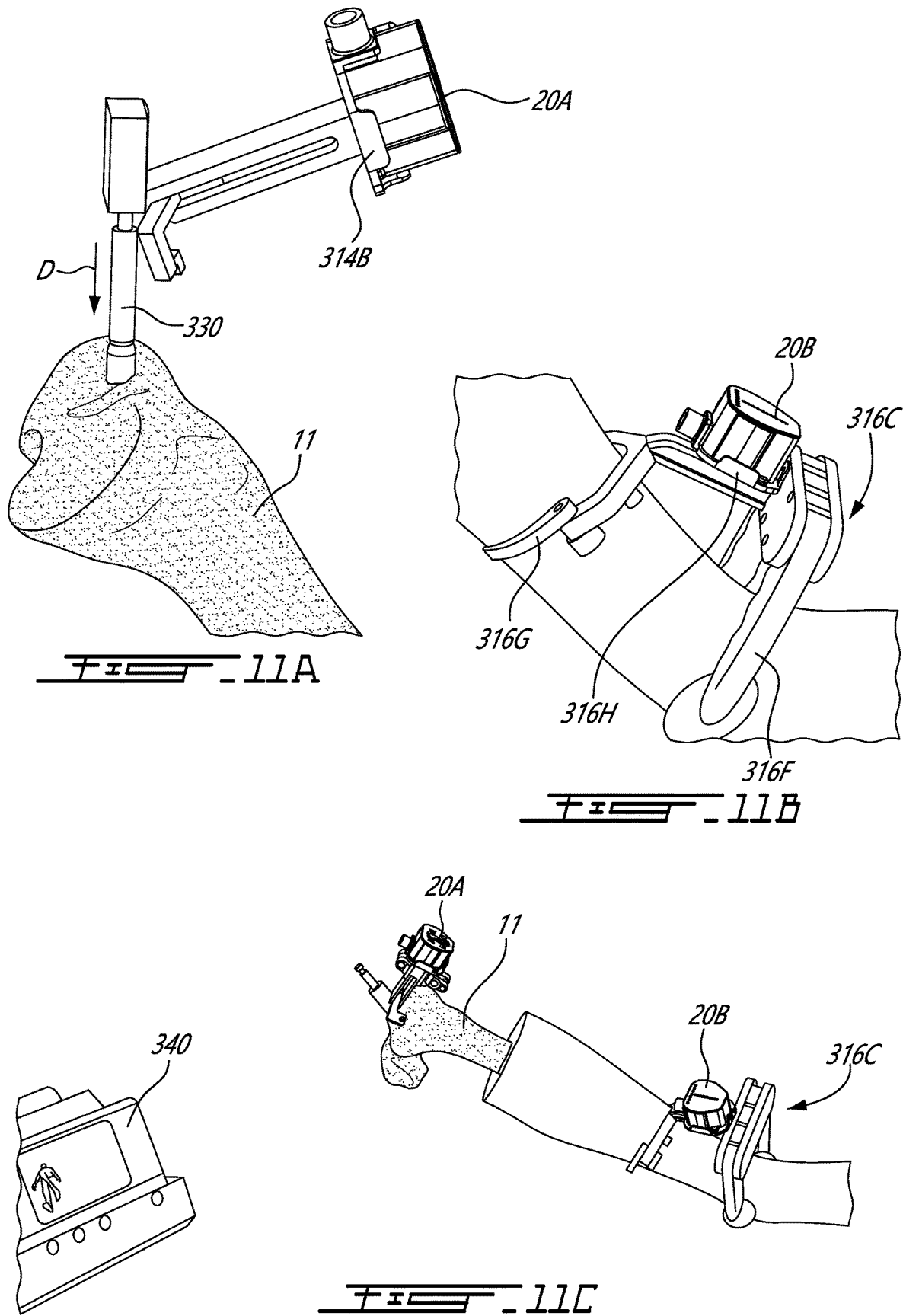

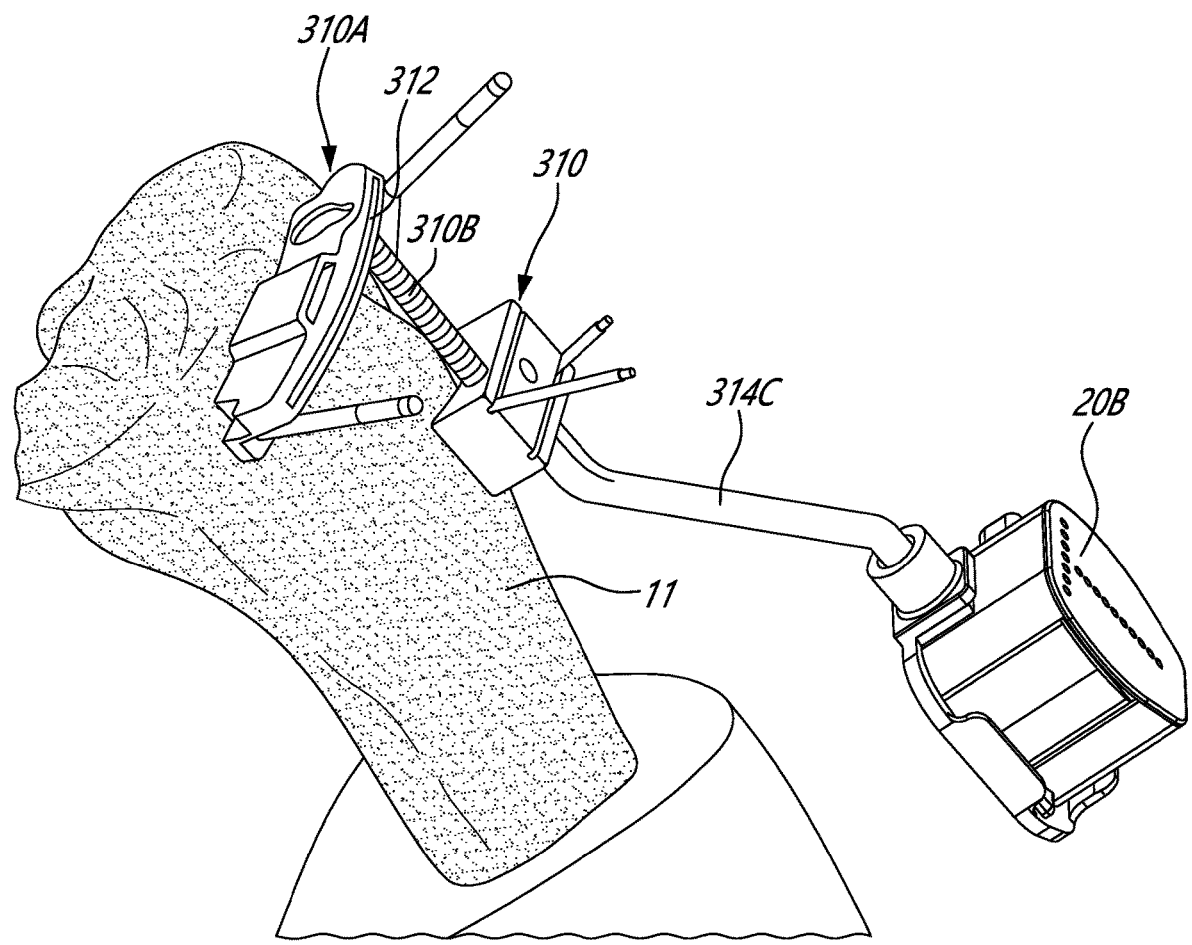

TIBIA CUTTING ASSEMBLY

CROSS-REFERENCE TO RELATED APPLICATIONS

This application is a continuation of U.S. patent application Ser. No. 16/007,270 filed Jun. 13, 2018 which claims priority to US provisional patent application having application Ser. No. 62/518,826 and filed Jun. 13, 2017, the entirety of both of which is hereby incorporated by reference.

TECHNICAL FIELD

The application relates generally to surgical guides and, more particularly, to a tibia cutting guide and assembly to plan a tibial cut in knee arthroscopy.

BACKGROUND

In computer-assisted surgery (CAS) systems which employ inertial-based or micro-electro-mechanical sensor (MEMS), trackable members continue to be developed. One of the principal steps in navigating a bone with inertial sensors is to determine a coordinate system of the bone relative to the sensors, so as to be able to determine the orientation of the bone. For the tibia, the orientation of the bone may be determined by its mechanical axis.

When traditional optical CAS navigation systems are used, the determination of the tibial mechanical axis can be achieved, for example, by using two optical bone sensors fixed to the bone at spaced apart locations, each optical sensor having six degrees of freedom (DOF) (i.e. 3 DOF in position and 3 DOF in orientation). When using trackable members having inertial sensors in an inertial-based CAS system, however, the inertial sensors do not necessarily provide six DOF. While the missing DOF can be calculated if necessary using integrated gyroscope and accelerometer readings, for example, a simpler and more efficient manner to digitize the mechanical axis of a tibia is nonetheless sought.

Therefore, there remains a need for an improved surgical tool which is used in conjunction with a CAS system in order to digitally acquire the mechanical axis of the tibia using readily identifiable anatomical reference points.

SUMMARY

In an aspect, there is provided a tibia cutting assembly, comprising: a tibia cut guide with at least one cut slot; a guide rod having a guide holder mountable to the cut guide at a first end of the guide rod, and a second end of the guide rod mountable non-invasively about a skin of a patient, the guide rod being extendable in length to displace the tibia cut guide and adjust a position thereof with respect to a tibia of the patient, and the guide holder cooperating with the tibia cut guide to adjust an orientation of the tibia cut guide; and at least one inertial sensor being mountable to the guide holder and being displaceable therewith to determine an orientation of the tibial cut guide relative to the guide rod.

In an embodiment, the guide holder includes for instance a guide mount being removably mountable to the tibia cut guide to be displaceable therewith, the guide mount extending from the tibia cut guide to a distal end of the guide mount, the distal end having a sensor bracket to receive the sensor, the sensor being displaceable with the guide mount and with the tibia cut guide.

In an embodiment, the guide holder includes for instance an anterior/posterior (AP) slider being removably mountable to the tibia cut guide to displace the tibia cut guide toward and away from the tibia.

In an embodiment, the guide holder includes for instance a guide adjustment mechanism mountable to the guide rod to adjust the orientation of the tibia cut guide along at least one of a medio-lateral axis and an anterior-posterior axis.

In an embodiment, the guide adjustment mechanism is for instance displaceable along the guide rod between the first and second ends thereof.

In an embodiment, the guide adjustment mechanism has for instance a locking device to arrest displacement of the guide adjustment mechanism along the guide rod.

In an embodiment, the assembly further comprises for instance a tibia pointer mountable to the first end of the guide rod, the tibia pointer extending from the first end of the guide rod to a distal end of the tibia pointer, the guide rod being extendable in length to abut the distal end of the tibia pointer against an upper portion of the tibia.

In an embodiment, the tibia pointer is for instance abuttable against the upper portion of the tibia to form a pivot point, the guide rod being pivotable about the pivot point.

In an embodiment, the guide rod is for instance pivotable about the pivot point to approximately visually align the guide rod with a mechanical axis of the tibia.

In an embodiment, further comprises for instance an ankle clamp disposed at the second end of the guide rod, the ankle clamp having clamp arms each having a clamp grip at a distal end of each clamp arm, each of the clamp grips being mountable to a skin of the patient about one of a malleolus of an ankle of the patient.

In an embodiment, the ankle clamp is for instance mounted to the second end of the guide rod at an ankle clamp joint, the ankle clamp being displaceable with respect to the second end of the guide rod.

In an embodiment, the ankle clamp has for instance an elongated slot, the ankle clamp joint having a protrusion inserted into the slot to mount the ankle clamp to the second end of the guide rod, a position of the ankle clamp with respect to the second end of the guide rod being adjustable by sliding the slot relative to the protrusion.

In an embodiment, the ankle clamp joint defines for instance a rotational axis about which the clamp arms are rotatable relative to the second end of the guide rod.

In an embodiment, the at least one inertial sensor is for instance displaceable along the guide rod to position the at least one inertial sensor in proximity to the second end of the guide rod.

In another aspect, there is provided a tibia cutting assembly, comprising: a tibia cut guide with at least one cut slot; a guide holder assembly having an anterior/posterior (AP) slider being removably mountable to the tibia cut guide to displace the tibia cut guide toward and away from a tibia of a patient, and a guide adjustment mechanism removably mountable to the AP slider to adjust an orientation of the tibia cut guide; a guide rod having opposed first and second ends, the guide holder assembly being mountable to the guide rod at the first end thereof, the second end of the guide rod being mountable non-invasively about a skin of the patient, the guide rod being extendable in length to adjust a position of the tibia cut guide with respect to the tibia of the patient; and a plurality of inertial sensors, a first sensor being mountable to the guide holder assembly, and a second sensor being mountable to the guide rod at the second end thereof.

In an embodiment, the guide holder assembly includes for instance a guide mount being removably mountable to the tibia cut guide to be displaceable therewith, the guide mount extending from the tibia cut guide to a distal end of the guide mount, the distal end having a sensor bracket to receive the first sensor, the first sensor being displaceable with the guide mount and with the tibia cut guide.

In an embodiment, the first sensor is for instance mountable to at least one of the AP slider and the guide adjustment mechanism of the guide holder assembly.

In an embodiment, the guide adjustment mechanism is for instance mountable to the guide rod to adjust the orientation of the tibia cut guide along at least one of a medio-lateral axis and an anterior-posterior axis.

In an embodiment, the guide adjustment mechanism is for instance displaceable along the guide rod between the first and second ends thereof.

In an embodiment, the guide adjustment mechanism has for instance a locking device to arrest displacement of the guide adjustment mechanism along the guide rod.

In an embodiment, the assembly further comprises for instance a tibia pointer mountable to the first end of the guide rod, the tibia pointer extending from the first end of the guide rod to a distal end of the tibia pointer, the guide rod being extendable in length to abut the distal end of the tibia pointer against an upper portion of the tibia.

In an embodiment, the tibia pointer is for instance abuttable against the upper portion of the tibia to form a pivot point, the guide rod being pivotable about the pivot point.

In an embodiment, the guide rod is for instance pivotable about the pivot point to approximately visually align the guide rod with a mechanical axis of the tibia.

In an embodiment, the assembly further comprises for instance an ankle clamp disposed at the second end of the guide rod, the ankle clamp having clamp arms each having a clamp grip at a distal end of each clamp arm, each of the clamp grips being mountable to a skin of the patient about one of a malleolus of an ankle of the patient.

In an embodiment, the ankle clamp is for instance mounted to the second end of the guide rod at an ankle clamp joint, the ankle clamp being displaceable with respect to the second end of the guide rod.

In an embodiment, the ankle clamp has for instance an elongated slot, the ankle clamp joint having a protrusion inserted into the slot to mount the ankle clamp to the second end of the guide rod, a position of the ankle clamp with respect to the second end of the guide rod being adjustable by sliding the slot relative to the protrusion.

In an embodiment, the ankle clamp joint for instance defines a rotational axis about which the clamp arms are rotatable relative to the second end of the guide rod.

In an embodiment, the at least one inertial sensor is for instance displaceable along the guide rod to position the at least one inertial sensor in proximity to the second end of the guide rod.

In another aspect, there is provided a tibia cutting assembly, comprising: a tibia cut guide with at least one cut slot; a guide rod; an ankle clamp at an end of the guide rod adapted to connect the tibia cutting assembly to an ankle; a connector at another end of the guide rod adapted to connect the tibia cutting assembly to a tibial plateau; a guide adjustment mechanism interfacing the tibia cut guide to the guide rod, the guide adjustment mechanism providing at least a first rotational joint to adjust a varus-valgus orientation of the tibia cut guide relative to a tibia, and a second rotational joint configured to adjust a flexion-extension orientation of the tibia cut guide relative to a tibia; and at least one inertial sensor being mountable to one of the tibia cut guide and the guide adjustment mechanism and being displaceable therewith to determine an orientation of the tibial cut guide relative to the guide rod.

In an embodiment, the guide adjustment mechanism has for instance a translational joint to displace the tibia cut guide along a direction parallel to an anterior-posterior axis of the tibia.

In an embodiment, the assembly further comprises for instance a translational joint between the guide adjustment mechanism and the guide rod.

DESCRIPTION OF THE DRAWINGS

Reference is now made to the accompanying figures in which:

FIGS. 1A to 4C are views of a tibia cutting assembly for effecting a resection operation on a tibia, according to an embodiment of present disclosure;

FIGS. 5 to 7C are views of a tibia cutting assembly for effecting a resection operation on a tibia, according to another embodiment of present disclosure;

FIGS. 8 to 10D are views of a tibia cutting assembly for effecting a resection operation on a tibia, according to another embodiment of present disclosure; and FIGS. 11A to 13 are views of a tibia cutting assembly for effecting a resection operation on a tibia, according to another embodiment of present disclosure.

DETAILED DESCRIPTION

Figure 1A:
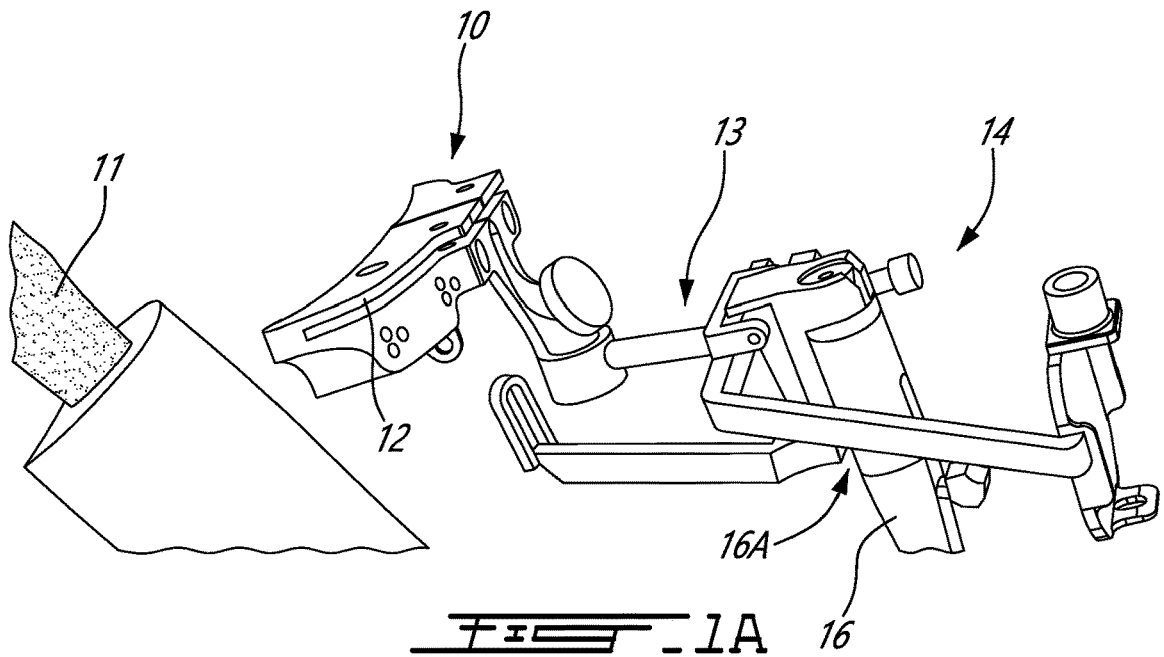
Figure 1B:
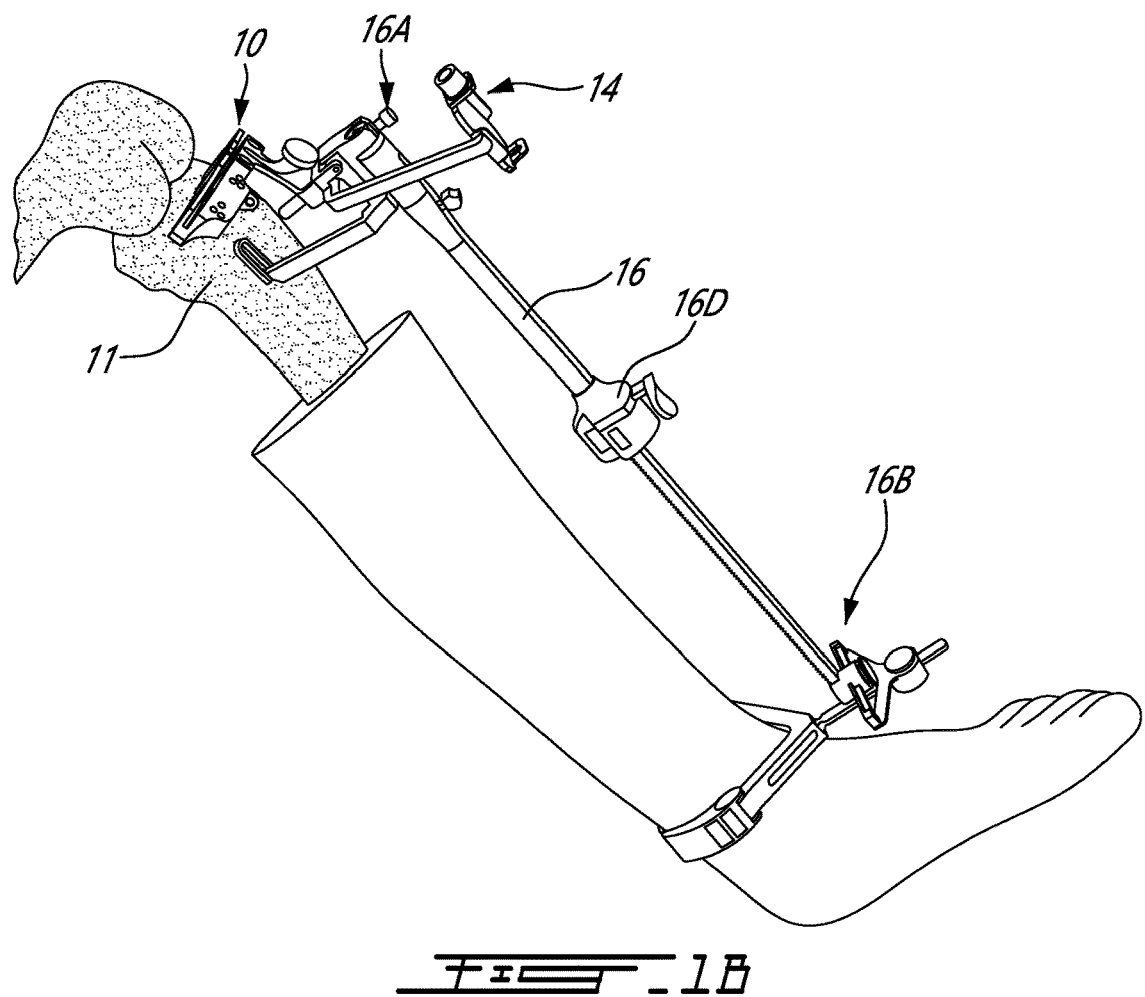

FIGS. 1A and 1B show a tibia cutting guide 10 used to guide a resection of a tibia 11 by a surgeon. The tibia cutting guide 10 has a cut slot 12 extending through the tibia cutting guide 10 (also referred to herein simply as "guide 10"). The cut slot 12 receives a resection tool therein, such as a flat saw blade, and guides its displacement to effect the resection of the tibia. In the depicted embodiment, the cut slot 12 is defined between two opposed planar surfaces to confine the resection tool to displace along a plane, whereby the resection of the tibia will create a tibial plane, also known as the tibial cut or proximal cut. The tibial plane may then support a tibial component, for example a metal plate anchored onto the tibial plane and a plastic spacer interfacing with a femoral component. The guide 10 is mounted to an orientation mechanism 13 of a guide holder 14. The orientation mechanism 13 functions to adjust the orientation of the guide 10 with respect to the tibia 11 in varus/valgus and slope. For example, the orientation mechanism 13 is connected to a remainder of the guide holder 14 by a pair of rotational joints, the axes of which are generally aligned with the medio-lateral axis for slope adjustment, and with the anterior-posterior (AP) axis for varus-valgus adjustment. In the depicted embodiment, the guide 10 is mounted to the guide holder 14 via a quick-release mechanism. The guide holder 14 is itself mounted to a guide rod 16 at a first end 16A of the guide rod 16. The guide rod 16 is an elongated body extending between the first end 16A and an opposed second end 16B. The guide rod 16 is adjustable in length.

Referring to FIG. 1B, with the guide 10 mounted to the guide holder 14 and the guide holder 14 mounted to the guide rod 16, the second end 16B of the guide rod 16 is mounted non-invasively about the skin S of the patient at the ankle A. In the depicted embodiment, the guide rod 16 has an ankle clamp 16C at the second end 16B which is used to clamp the second end 16B of the guide rod 16 to the ankle. This locates the second end 16B of the guide rod 16 adjacent to a distal end of the tibia 11. With the guide rod 16 mounted to the patient at its second end 16B, the length of the guide rod 16 can be adjusted to approximate the length of the tibia 11 of the patient. In the depicted embodiment, the guide rod 16 has a telescopic joint 16D. The telescopic joint 16D joins and locks two segments of the guide rod 16 together, and allows at least one of the segments to be displaced relative to the other to increase the overall length of the guide rod 16.

Figure 2A:
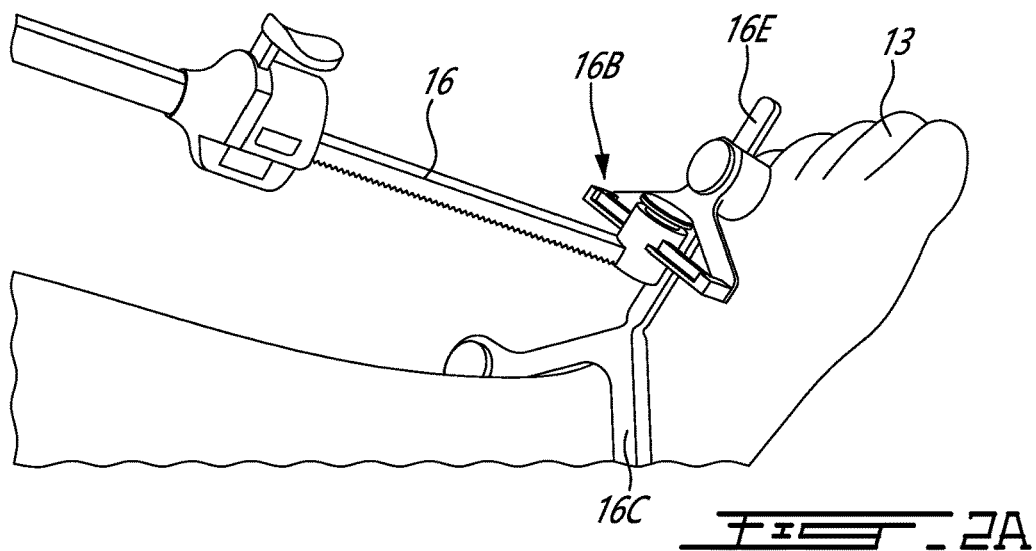

Referring to FIG. 2A, the second end 16B of the guide rod 16 can be aligned with a patient landmark. In the depicted embodiment, a pointer 16E is attached to the guide rod 16 at the second end 16B. The pointer 16E is moved to align it with any suitable landmark. Displacement of the point 16E causes displacement of the guide rod 16. For example, the pointer 16E may be aligned with the second toe T of the patient's foot F. By aligning the pointer 16E and thus the guide rod 16 with the second toe T of the foot F, the guide rod 16 is generally located at an approximate midpoint of the ankle A, which typically corresponds with a location of the mechanical axis of the tibia 11. In an embodiment, the guide rod 16 is mounted to the ankle clamp 16C at a translational joint that is displaceable in a direction generally parallel to a line joining the malleoli of the ankle A.

Figure 2B:
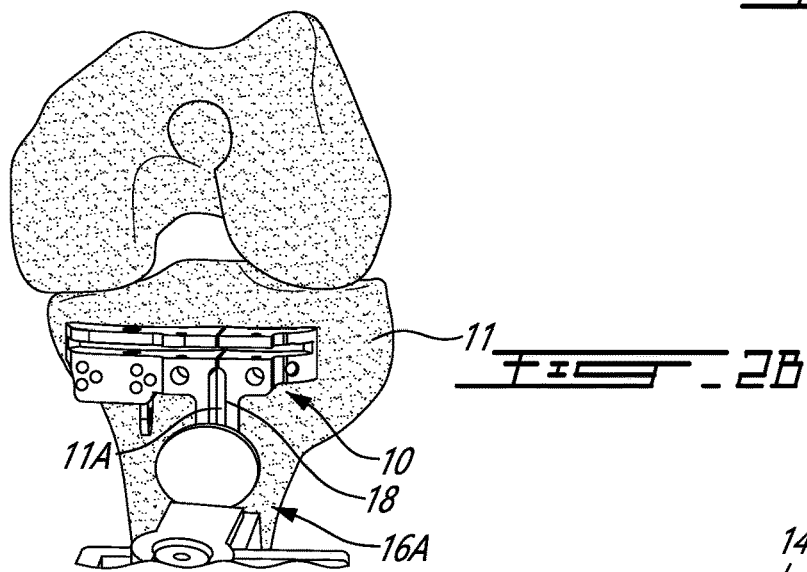
Figure 2C:
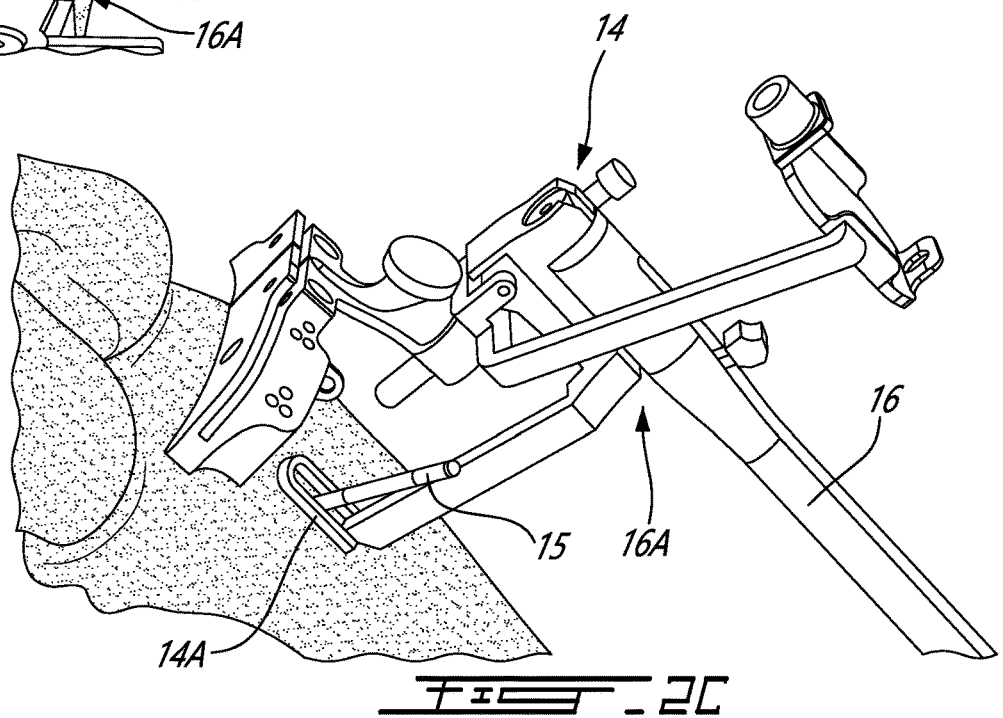

At the other, first end 16A of the guide rod 16, and referring to FIG. 2B, the guide 10 is aligned with a visual bone landmark of the tibia 11. In the depicted embodiment, the guide 10 is displaced by the orientation mechanism 13 to align a vertical slot 18 in the guide 10 with the ⅓ mark of the tibial tubercle 11A. The guide 10 is aligned with another bone landmark of the tibia 11 in other embodiments. Once the vertical slot 18 is properly aligned, the guide holder 14 can be secured to the tibia 11. In the embodiment shown in FIG. 2C, a pin 15 is inserted through a pin hole 14A of the guide holder 14. The pin 15 secures the guide holder 14 to the tibia 11. The guide rod 16 is now mounted in place at both of its first and second ends 16A, 16B, and is generally aligned with the mechanical axis of the tibia 11.

Figure 3A:
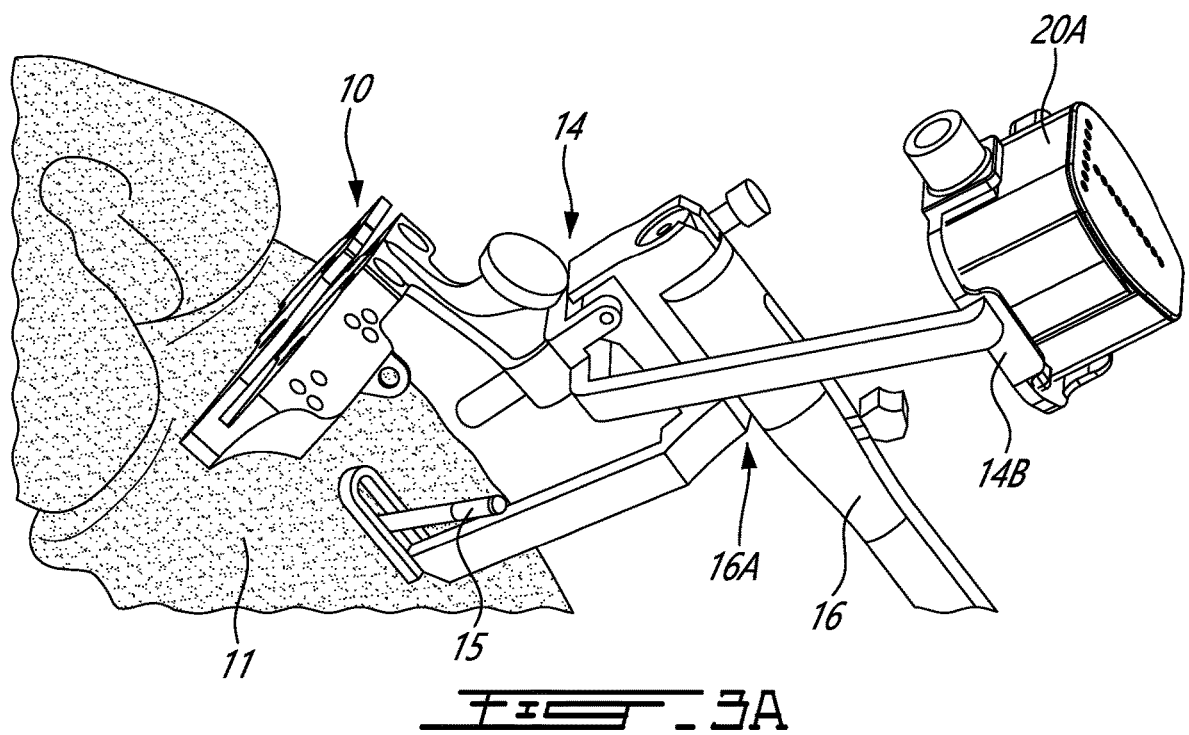
Figure 3B:
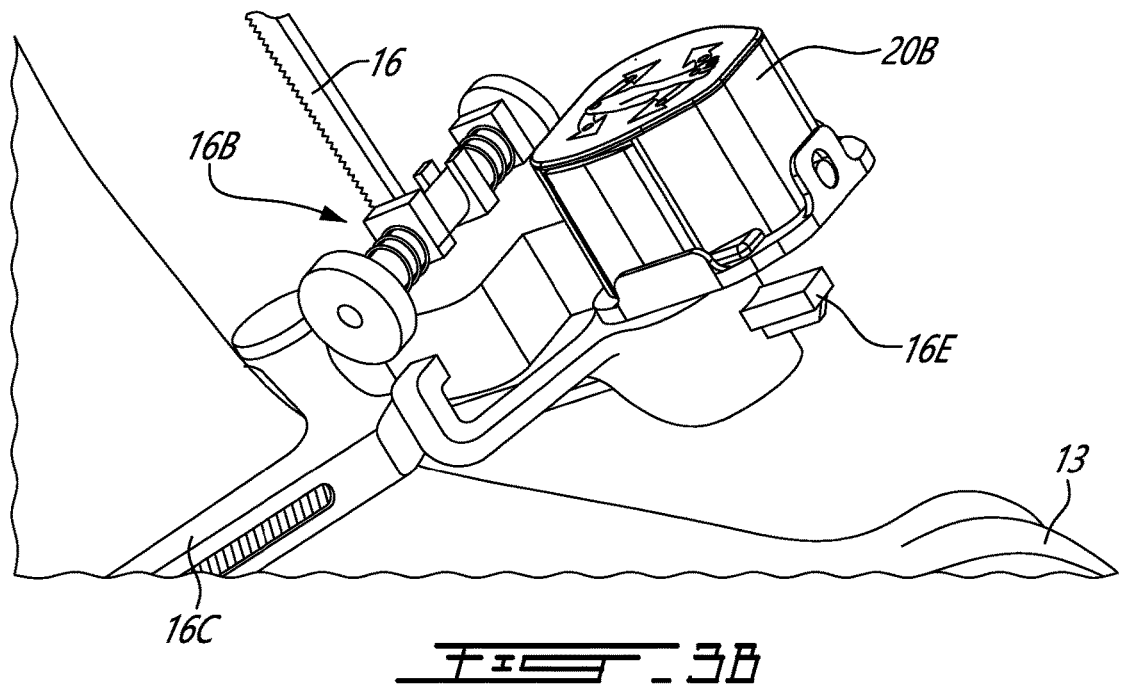

With the guide rod 16 held parallel to the tibia 11, the slope of the guide rod 16 with respect to the tibia 11 can be adjusted as desired. Inertial sensors can also be provided, as shown in FIG. 3A. In the depicted embodiment, a first inertial sensor 20A is mounted to a sensor bracket 14B of the guide holder 14. The sensor bracket 14B moves with the orientation mechanism 13, and thus with the cutting guide 10. Since the guide holder 14 is attached with the pin 15 to the tibia 11, the first inertial sensor 20A mounted to the guide holder 14 is indirectly mounted to the tibia 11 and in fixed relationship therewith. Referring to FIG. 3B, a second inertial sensor 20B is mounted at the second end 16B of the guide rod 16 to the ankle clamp 16C. Since the pointer 16E is aligned with the second toe T, and thus the guide rod 16 is aligned with the midpoint of the ankle A, the second inertial sensor 20B is similarly aligned with the ankle A. The second inertial sensor 20B therefore serves as a tibia reference, representative for example of the mechanical axis of the tibia 11. The inertial sensors 20A, 20B are sensors that are capable of detecting their own motion without the use of an external reference frames.

The orientation of the guide 10 with respect to the tibia 11 can now be adjusted based on data from the inertial sensors 20A, 20B. This allows the surgeon to achieve the orientation of the guide 10 that is desired for the resection to be effected. Referring to FIG. 4A, the orientation mechanism 13 is used for adjusting the orientation of the guide 10 mounted to the guide holder 14, with the second inertial sensor 20B moving concurrently with the guide 10. In the depicted embodiment, the orientation mechanism 13 includes a first screw 22A for performing varus-valgus adjustments of the guide 10, and a second screw 22B for performing slope adjustments of the guide 10.

Referring to FIG. 4B, with an orientation of the guide 10 set, a stylus 24 is inserted into the cut slot 12 to adjust the resection level. The guide 10 is then secured into place on the tibia 11, for example by pinning the guide 10 to the tibia 11. The guide rod 16 and the guide holder 14 are then removed, leaving only the cutting guide 10 in place on the tibia 11, as shown in FIG. 4C. The surgeon can now effect the resection operation.

Figure 5:
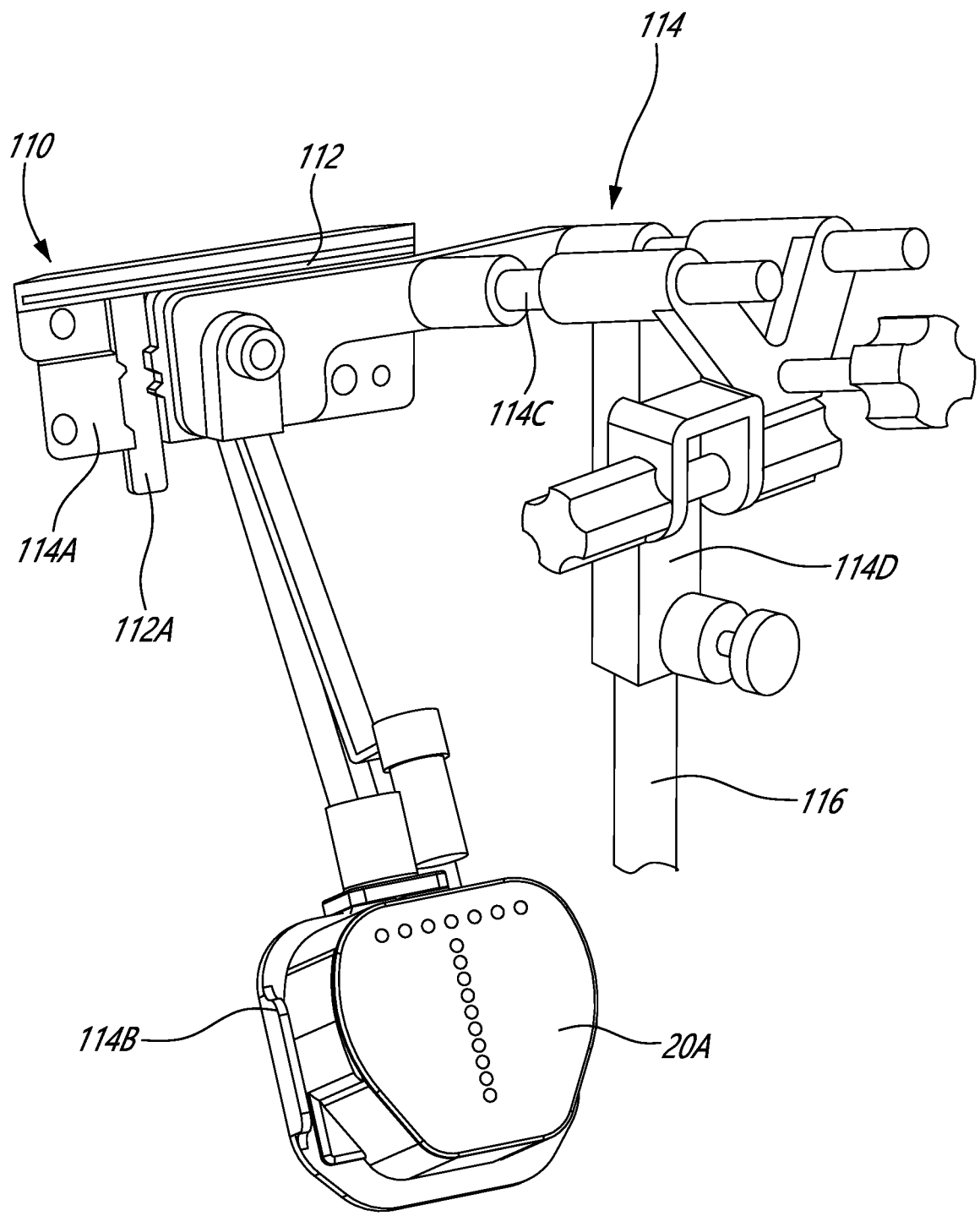

Another embodiment of the tibia cutting guide 110, the guide holder 114, and the guide rod 116 is shown in FIGS. 5 to 7C, and is collectively referred to as a tibia cutting assembly 100. Referring to FIG. 5, the cut slot 112 of the cutting guide 110 has a substantially planar configuration to guide a planar resection of the tibia. The cutting guide 110 may be sized for the planar resection to be partial or complete. Partial resection entails removing only a portion of the tibial plateau, e.g., the portion of the plateau on the lateral condyle or on the medial condyle. The cutting guide 110 in FIG. 5 may have one or more mounting legs 112A which engage with the guide holder 114 to mount the cutting guide 110 to the guide holder 114. The guide holder 114 in FIG. 5 is an assembly of different components. One of the components of the guide holder 114 includes a guide mount 114A having one or more slots or receptacles to receive therein the mounting legs 112A of the guide 110, although other connection configurations are contemplated as alternatives to legs and slots/receptacles. The mounting legs 112A are secured in the slots to mount the guide 110 to the guide mount 114A. The guide mount 114A is an elongated body and has a sensor bracket 114B at a distal end for receiving the first inertial sensor 20A. The guide mount 114A and the sensor bracket 114B are integrally connected—for instance by being a monoblock component—and therefore move concurrently.

Another component of the guide holder 114 of FIG. 5 is an anterior/posterior (AP) slider 114C. The AP slider 114C is mounted to the guide mount 114A. In an alternate embodiment, the AP slider 114C is mounted directly to the guide rod 116. The AP slider 114C allows a translational movement, to displace the cutting guide 110 closer or away from the tibia 11. Another component of the guide holder 114 is a guide adjustment mechanism 114D which is mounted to the AP slider 114C. The guide adjustment mechanism 114D helps to adjust the orientation of the guide 110 before the resection operation, by having two rotational joints, respectively aligned with the medio-lateral axis for slope adjustment, and with the AP axis for varus-valgus adjustment. The guide holder 114 of FIG. 5 is shown in a fully assembled configuration, and components can be mounted onto the guide rod 116.

Referring to FIG. 6A, the first component mounted onto the guide rod 116 may be the second inertial sensor 20B. The second inertial sensor 20B may be received in sensor bracket 119 (FIG. 7C) which may be slid along the outside surface of the guide rod 116 to position the second inertial sensor 20B in proximity to the ankle clamp 116C of the guide rod 116 at the second end 116B of the guide rod 116. The ankle clamp 116C is of the type that may have malleolus pads for being mounted on the malleoli. The second inertial sensor 20B serves as a tibia reference, using for example the alignment with the malleolus line extending between the malleoli. Referring to FIG. 6B, components are then positioned at the first end 116A of the guide rod 116. The guide holder 114 is mounted to the guide rod 116 by sliding the first end 116A of the guide rod 116 through a mounting slot in the guide adjustment mechanism 114D, concurrently forming a translational joint. After the guide holder 114 is mounted onto the guide rod 116, an axis pointer 118 with a spike 118A is also mounted onto the guide rod 116 at its first end 116A. The guide 110, guide holder 114, and guide rod 116 are now ready to be mounted to the patient's anatomy.

Referring to FIG. 6C, the ankle clamp 116C of the guide rod 116 is mounted to the skin S about the malleoli of the patient. The guide rod 116 and components mounted thereon are then centered to approximately visually align with the longitudinal mechanical axis of the tibia 11. The length of the guide rod 116 can be adjusted to approximate the length of the tibia 11. In the depicted embodiment, the length of the guide rod 116 can be adjusted telescopically, or by having the various components mounted to slide on the guide rod 116. The location of the guide holder 114 on the guide rod 116 can also be modified by sliding the guide adjustment mechanism 114D along the guide rod 116, for the cutting guide 110 to be approximately placed at a desired cut location.

To mount the first end 116A of the guide rod 116 to the tibia 11, and as shown in FIG. 6C, the surgeon drives the spike 118A of the axis pointer 118 at the mechanical axis entry point of the tibia 11. The guide rod 116 can then be rotated about the spike 118A to align the guide rod 116 with a visual bone landmark of the tibia 11. In the depicted embodiment, the guide holder 114 is rotated with the guide rod 116 to align the guide holder 114 with the ⅓ mark of the tibial tubercle 11A. The axis pointer 118 therefore serves as a connector between the tibial plateau and the guide rod 116.

Once the guide holder 114 is properly aligned, the guide rod 116 can be set in a fixed position relative to the tibia 11. In the depicted embodiment, the ankle clamp 116C of the guide rod 116 is tightened about the malleoli of the ankle. A pin or other fastener can also be inserted to secure the axis pointer 118 to the tibia 11 and prevent rotation of the guide rod 116. Navigation tracking may then be started by activating the inertial sensors 20A, 20B. The orientation of the guide 110 with respect to the tibia 11 can then be adjusted based on data from the inertial sensors 20A, 20B, as described above, with the rotational joints of the guide adjustment mechanism 114D. Once an appropriate varus/valgus and/or slope are obtained, the guide 110 can be displaced toward the tibia 11 by sliding the guide mount 114A and AP slider 114C relative to the guide adjustment mechanism 114D.

Figure 7A:
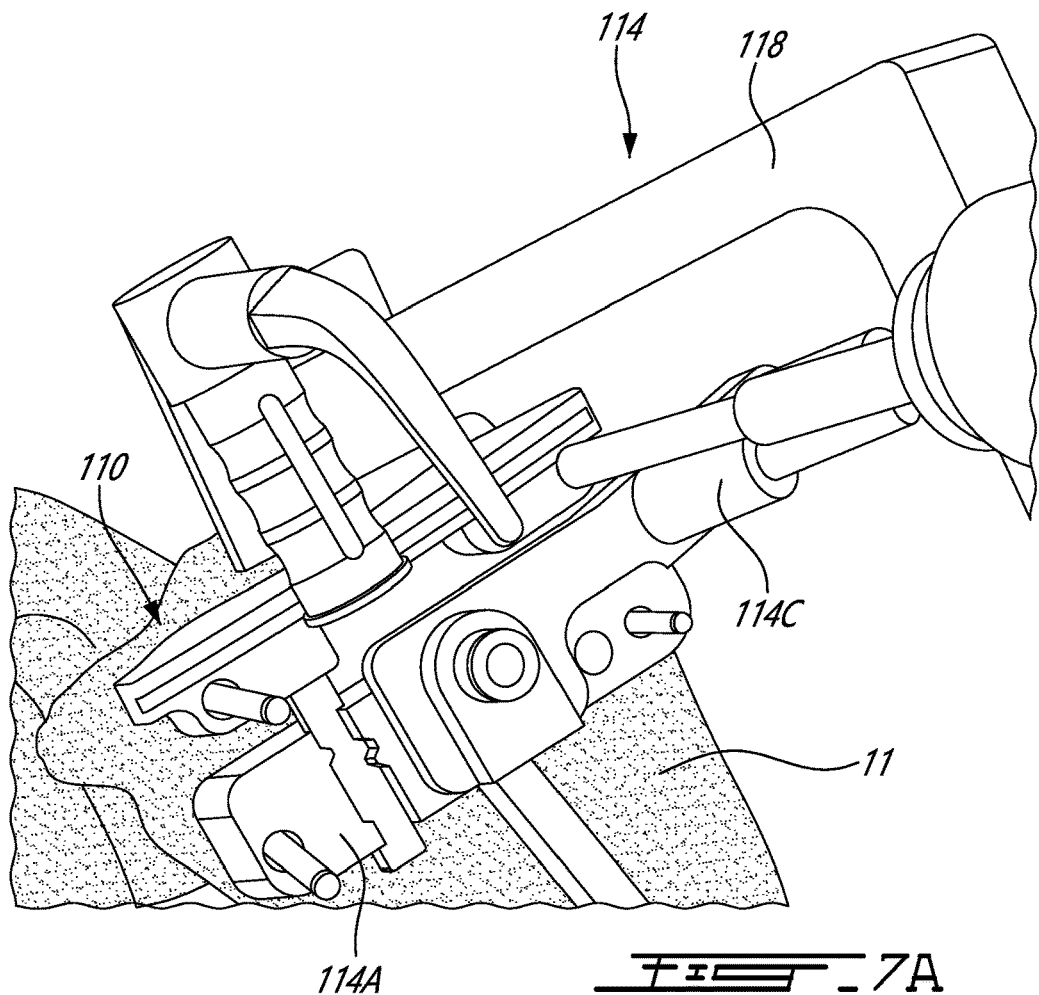
Figure 7B:
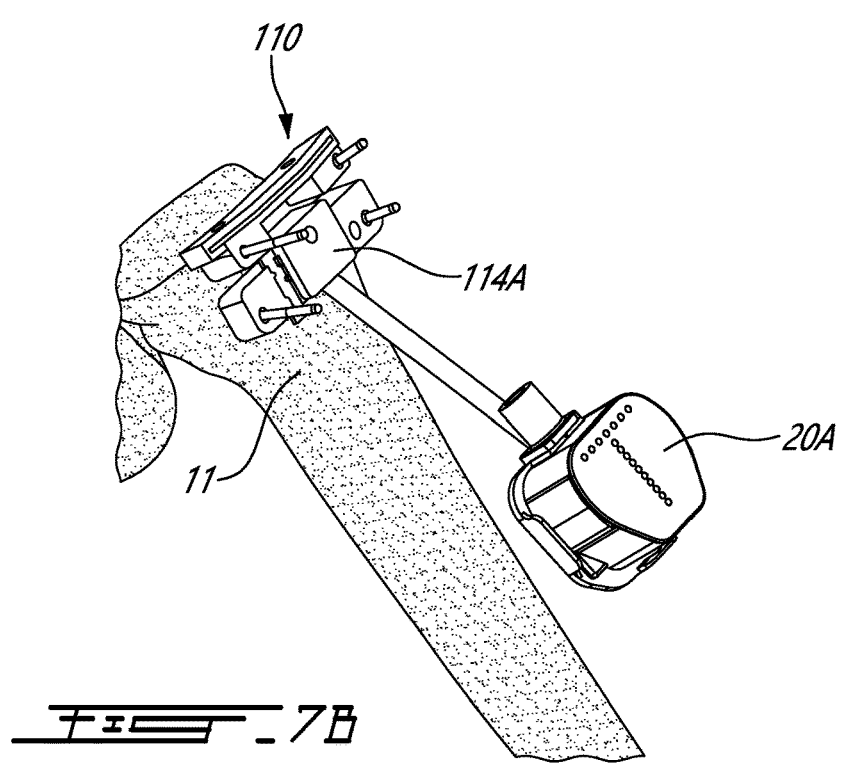

Referring to FIG. 7A, with the guide 110 in position and its resection level adjusted, the guide mount 114A is secured to the tibia 11 with one or more pins. The guide 110 itself may also be secured to the tibia 11 with one or more pins. With the guide 110 being securely mounted to the tibia 11, some of the components of the guide holder 114 are removed from the guide 110. In the depicted embodiment, the AP slider 114C is removed from the guide mount 114A. The fasteners securing the axis pointer 118 to the tibia 11 may be removed in order to remove the axis pointer 118 from the tibia 11. The guide rod 116 is removed from the malleoli, leaving only the cutting guide 110 attached to the tibia 11, and the guide mount 114A with the first inertial sensor 20A attached to the guide 110, as shown in FIG. 7B. The surgeon can now effect the resection operation.

FIG. 7C shows the tibia cutting assembly 100 in an assembled state. The axis pointer 118 includes an axis pointer bracket 118B with apertures therein. The axis pointer 118 is mounted to the guide rod 116 by inserting the first end 116A of the guide rod 116 through the apertures of the axis pointer bracket 118B, thereby forming a translation joint. The AP slider 114C is mounted to the guide mount 114A, and allows for it and the cutting guide 110 to displace along a direction parallel to the sagittal or AP axis 111. The AP slider 114C may have a mounting arm 115A with a distal end mounted to the cutting guide 110 directly, or to the guide mount 114A. A proximal end of the mounting arm 115A is attached to a displacement tab 115B with a locking mechanism 115C. The locking mechanism 115C is operatively connected to two displacement bars 115D, which are each housed within sleeves 117A of the guide adjustment mechanism 114D, to displace the displacement bars 115D relative to the sleeves 117A along a translational direction aligned with the AP axis 111. When a user wishes to displace the AP slider 114C along the AP axis 111, to thereby effect displacement of the cutting guide 110 along the AP axis 111, the user depresses the displacement tab 115B to unlock the locking mechanism 115C. However, the system may be without such locking mechanism as well. The user is thereby able to slide the displacement bars 115D relative to the sleeves 117A by pushing or pulling along the displacement tab 115B, thereby causing displacement of the cutting guide 110 along a direction parallel to the AP axis 111 toward or away from the tibia.

Still referring to FIG. 7C, the guide adjustment mechanism 114D in the depicted embodiment includes a mounting bracket 117B with apertures therein. The guide adjustment mechanism 114D is mounted to the guide rod 116 by inserting the first end 116A of the guide rod 116 through the apertures of the mounting bracket 117B, thereby forming a translational joint. The mounting bracket 117B has a lever 117C (e.g., quick-release lever with cam surface) which is actionable by a user to tighten and loosen an engagement of the mounting bracket 117B with the outer surface of the guide rod 116. By actuating the lever 117C to loosen the engagement of the mounting bracket 117B with the guide rod 116, the user is able to displace the guide adjustment mechanism 114D, and thus the cutting guide 110, along the guide rod 116. The selected position of the guide adjustment mechanism 114D on the guide rod 116 is secured by actuating the lever 117C to tighten the engagement of the mounting bracket 117B with the guide rod 116. The guide adjustment mechanism 114D in the depicted embodiment may have a first rotational joint 117D which includes a bracket 117E including or attached to the sleeves 117A, and a first knob 117F connected to a rotatable shaft 117G which engages the bracket 117E, the bracket 117E being rotatably mounted to a remainder of the guide adjustment mechanism 114D at axis 111A. The first rotational joint 117D allows the AP slider 114C, and thus the guide mount 114A and the cutting guide 110, to rotate about axis 111A, and thereby achieve a slope adjustment of the cutting guide 110, i.e., the adjustment of the orientation of the cut plane in rotation about the medio-lateral axis. For example, the slope may be angled downwardly in posteriorly. To effect this rotation about the axis of the guide rod 116, the first knob 117F is rotated in either direction to cause a rotation of the bracket 117E about axis 111A, which axis 111A is generally parallel to the medio-lateral axis of the patient during surgery. This allows the bracket 117E and the sleeves 117A to rotate, thereby causing the displacement bars 115D to also rotate, to in turn rotate the remainder of the AP slider 114C and the cutting guide 110. The guide adjustment mechanism 114D is therefore able to adjust the cut guide 110 along a flexion-extension orientation relative to a tibia. The guide adjustment mechanism 114D in the depicted embodiment may have a second rotational joint 117H which includes a bracket 117I moving with the bracket 117E (or integral with it) and a second knob 117J. The second rotational joint 117H allows the AP slider 114C, and thus the guide mount 114A and the cutting guide 110, to rotate about the anterior-posterior axis 111B to adjust the varus-valgus angle of the cutting guide 110 relative to the tibia. To effect this rotation about the anterior-posterior axis 111B, the second knob 117J is rotated in either direction, which allows the bracket 117E and the sleeves 117A to rotate about the anterior-posterior axis, as axis 111B is generally parallel with the anterior-posterior axis of the tibia, thereby causing the displacement bars 115D to rotate, to in turn rotate the remainder of the AP slider 114C and the cutting guide 110. According to an embodiment, the second knob 117J has an endless screw portion engaged with a fixed gear on a remainder of the guide adjustment mechanism 114D. Accordingly, a rotation of the knob 117J will result in a fine adjustment of the orientation of the bracket 117I about axis 111B.

Still referring to FIG. 7C, a second sensor bracket 119 for receiving the second inertial sensor 20B may be mounted about the outer surface of the guide rod 116. The second sensor bracket 119 may be displaceable along the guide rod 116 between the first and second ends 116A, 116B by way of a translational joint therebetween, and it may be fixedly attached to the guide rod 116. The second inertial sensor 20B is therefore displaceable along the guide rod 116 to position the second inertial sensor 20B in proximity to the second end 116B of the guide rod 116, as shown in FIG. 7C, and to position it in proximity to the ankle clamp 116C.

As shown in FIG. 7C, the ankle clamp 116C is located at the second end 116B of the guide rod 116. The ankle clamp 116C has two clamp arms 120A each having a clamp grip 120B at a distal end. The clamp arms 120A and the clamp grips 120B are manipulable to be displaced toward and away from the skin of the patient. Each clamp grip 120B is configured to engage the skin about one of the malleoli of an ankle of the patient. The grips 120B may be cups as shown, but may also have other configurations including pointy ends. When the clamp grips 120B are mounted to the skin about the malleoli of the patient, a line between the clamp grips 120B represents or approximates a malleolus line, which is a line extending between the malleoli. The clamp grips 120B therefore provide a tibia reference (i.e. the malleolus line), which can be used by the second inertial sensor 20B. The position and orientation of the ankle clamp 116C is adjustable. The ankle clamp 116C is mounted to the second end 116B of the guide rod 116 at an ankle clamp joint 121. The ankle clamp joint 121 includes a mount arm 121A extending between a distal end attached to the second end 116B of the guide rod 116, and a proximal end attached to a pivot bracket 121B. The pivot bracket 121B includes a protrusion 121C which is inserted into an elongated slot 121D to mount the ankle clamp 116C to the second end 116B of the guide rod 116. The ankle clamp 116C is displaceable with respect to the second end 116B of the guide rod 116 with the ankle clamp joint 121. More particularly, a position of the ankle clamp 116C with respect to the second end 116B of the guide rod 116 is adjustable by sliding the protrusion 121C within the slot 121D. The ankle clamp joint 121 also defines a rotational axis RA about which the clamp arms 120A are rotatable relative to the second end 116B of the guide rod 116. The pivot bracket 121B defines the rotational axis RA in the depicted embodiment, and includes a knob 121E to selectively allow pivoting of the clamp arms 120A. The clamp arms 120A are displaceable toward and away from each other, in a direction substantially parallel to the elongated slot 121D, to vary the distance between the clamp arms 120A and accommodate ankles of different sizes.

Still referring to FIG. 7C, the length of the guide rod 116 can be adjusted to approximate the length of the tibia 11. In the depicted embodiment, the length of the guide rod 116 can be adjusted telescopically. For example, the guide rod 116 may include an inner rod segment nested within an outer rod segment, where the inner and outer rod segment are displaceable relative to each other to vary the length of the guide rid 116. Navigation tracking is then started by activating the inertial sensors 20A, 20B. The orientation of the guide 110 with respect to the tibia 11 can then be adjusted based on data or feedback from the inertial sensors 20A, 20B, by adjusting the position of the cutting guide 110 using one or more of the AP slider 114C and the guide adjustment mechanism 114D, as described above.

Another embodiment of the tibia cutting assembly 200 is shown in FIGS. 8 to 10D, and includes the tibia cutting guide 210, the guide holder 214, and the guide rod 216. Referring to FIG. 8, the cut slot 212 of the cutting guide 210 has a substantially planar configuration to guide a planar resection of the tibia. The guide holder 214 in FIG. 8 is an assembly of different components. One of the components of the guide holder 214 of FIG. 8 is an anterior/posterior (AP) slider 214C, for translating the cutting guide 210 toward or away from the tibia. The AP slider 214C is mounted to the guide 210. Another component of the guide holder 214 is a guide adjustment mechanism 214D which is mounted to the AP slider 214C, for adjusting the orientation of the cutting guide 210 relative to the tibia, in slope and varus-valgus. In the depicted embodiment, the AP slider 214C is slid onto the guide adjustment mechanism 214D to mount the cutting guide 210 to the guide adjustment mechanism 214D. The guide adjustment mechanism 214D helps to adjust the orientation of the guide 210 before the resection operation. After the guide holder 214 is mounted onto the guide rod 216, a tibia pointer 218 is mounted onto the guide holder 214 at the first end 216A of the guide rod 216. The tibia pointer 218 has a screw attachment 218A that is rotated to mount the tibia pointer 218 to the guide adjustment mechanism 214D. The ankle clamp 216C is mounted to the other, second end 216B of the guide rod 216. The guide 210, guide holder 214, and guide rod 216 as assembled in the manner shown in FIG. 8 are now ready to be mounted to the patient's anatomy.

Figure 9:
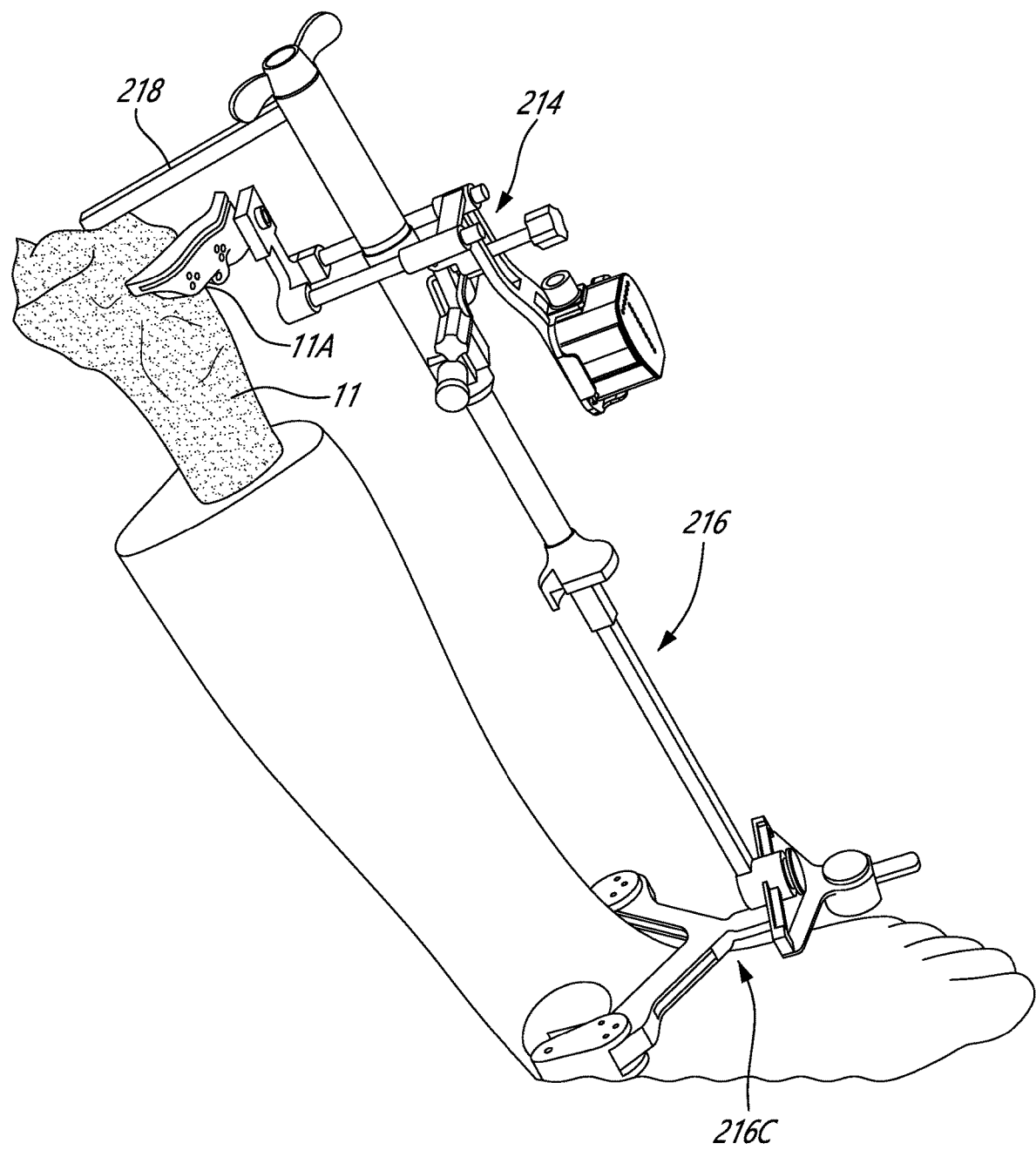

Referring to FIG. 9, the ankle clamp 216C of the guide rod 216 is mounted to the skin S about the malleoli of the ankle A. The guide rod 216 and components mounted thereon are then centered to approximately visually align with the longitudinal mechanical axis of the tibia 11. The length of the guide rod 216 can be adjusted to approximate the length of the tibia 11. In the depicted embodiment, the length of the guide rod 216 is adjusted until the tibia pointer 218 abuts against an upper portion of the tibia 11, as shown in FIG. 9. The guide rod 216 can then be rotated about the point of contact between the tibia pointer 218 and the tibia 11 to align the guide rod 216 with a visual bone landmark of the tibia 11. In the depicted embodiment, the guide holder 214 is rotated with the guide rod 216 to align the guide holder 214 with the ⅓ mark of the tibial tubercle 11A. A pin or other fastener can also be inserted to secure the tibia pointer 118 to the tibia 11 and prevent rotation of the guide rod 216. The tibia pointer 218 therefore serves as a connector between the tibial plateau and the guide rod 216.

Figure 10A:
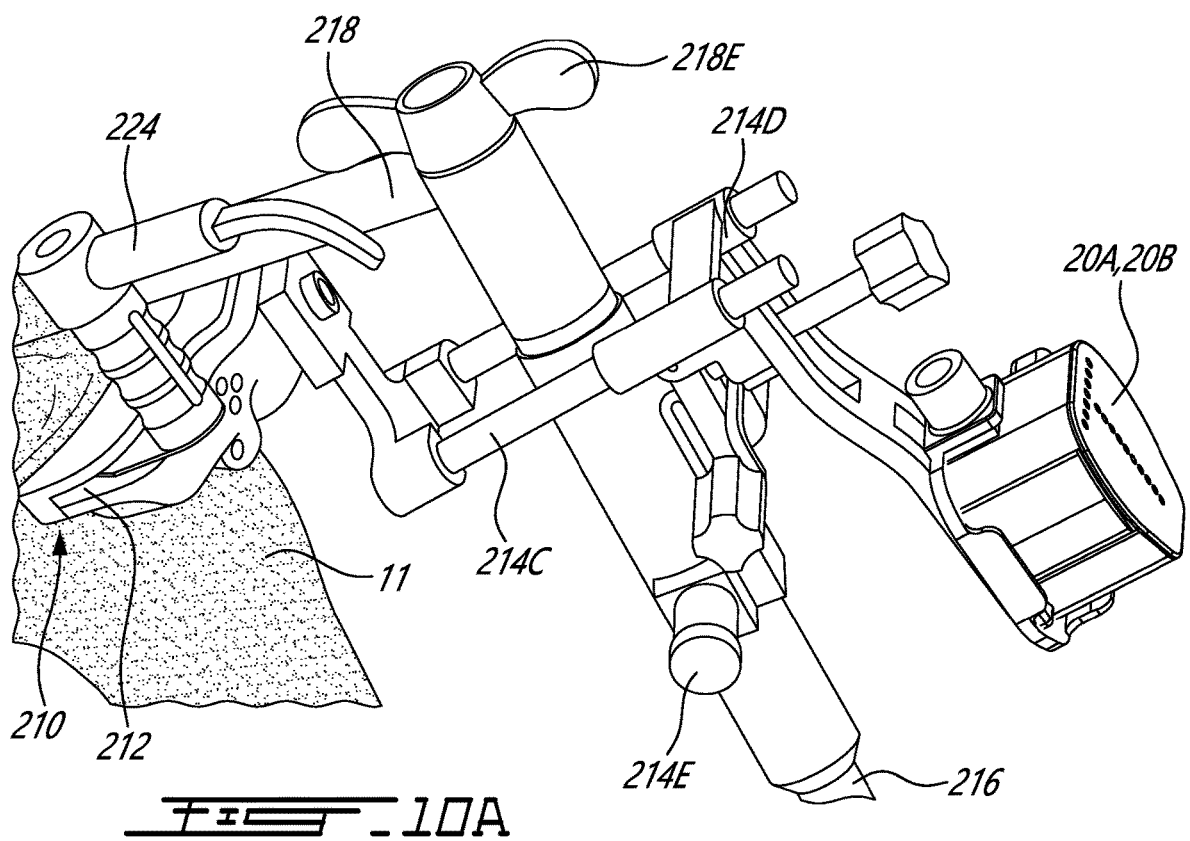

Referring to FIG. 10A, navigation tracking is started by activating one or both of the inertial sensors 20A, 20B. The orientation of the guide 210 with respect to the tibia 11 can then be adjusted based on data from the inertial sensors 20A, 20B, as described above using the rotational joints of the guide adjustment mechanism 114D. Once an appropriate varus/valgus is obtained, the guide 210 can be displaced toward the tibia 11 by sliding the AP slider 214C relative to the guide adjustment mechanism 214D. A stylus 224 is inserted into the cut slot 212 of the guide 210 to adjust the resection level. The guide 210 is now in the proper position for resection. The surgeon locks the height of the guide 210 with a locking device 214E on the guide adjustment mechanism 214D. In the depicted embodiment, the locking device 214E includes a screw that can be tightened to fix the height of the guide adjustment mechanism 214D on the guide rod 216, thereby fixing the height of the guide 210 mounted to the guide holder 214.

Figure 10B:
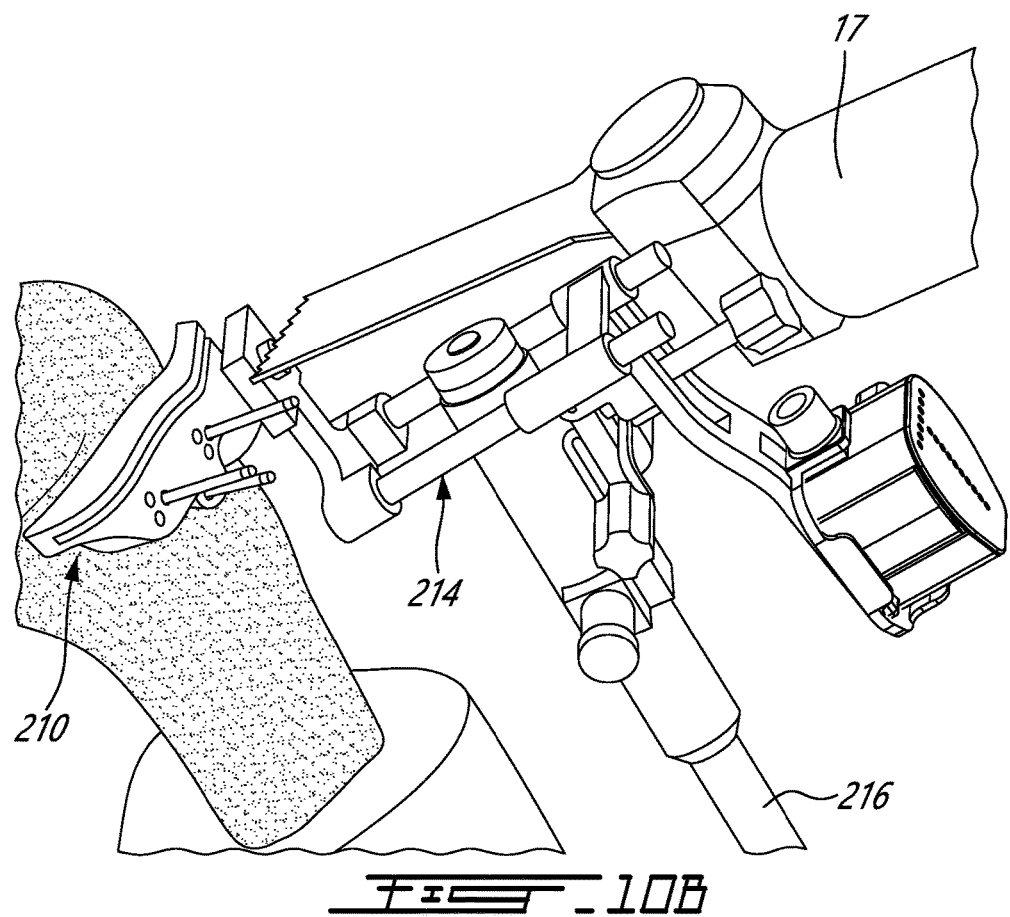

The guide 210 is then secured into place on the tibia 11, for example by pinning the guide 210 to the tibia 11. In the depicted embodiment, only a single component is removed prior to performing the resection operation, as shown in FIG. 10B. In the depicted embodiment, the screw attachment 218A of the tibia pointer 218 is loosened to remove the tibia pointer 218 from the guide adjustment mechanism 214D, leaving the cutting guide 210, the guide holder 214, and the guide rod 216 in place on the tibia 11. The surgeon can now effect the resection operation with a resection tool 17 having a resection blade 17A.

FIG. 10O shows the tibia cutting assembly 200 in an assembled state. The AP slider 214C is mounted directly to the cutting guide 210 to displace the cutting guide 210 along a direction parallel to the sagittal or AP axis 221. The AP slider 214C has a displacement tab 215B with a locking mechanism 215C. The locking mechanism 215C is operatively connected to two displacement bars 215D, which are each housed within sleeves 217A of the guide adjustment mechanism 214D, to displace the displacement bars 215D relative to the sleeves 217A. When a user wishes to displace the AP slider 214C along the AP axis 221, to thereby effect displacement of the cutting guide 210 along the AP axis 221, the user depresses the displacement tab 215B to unlock the locking mechanism 215C. However, the system may be without such locking mechanism as well. The user is thereby able to slide the displacement bars 215D relative to the sleeves 217A by pushing or pulling along the displacement tab 215B, thereby causing displacement of the cutting guide 210 along a direction parallel to the AP axis 221 toward or away from the tibia.

Still referring to FIG. 10O, the guide adjustment mechanism 214D in the depicted embodiment includes a mounting bracket 217B. The guide adjustment mechanism 214D in the depicted embodiment has a first rotational joint 217D which includes a bracket 217E including or attached to the sleeves 217A, and a first knob 217F connected to a rotatable shaft which engages the bracket 217E, the bracket 217E being rotatably mounted to a remainder of the guide adjustment mechanism 214D at axis 211A. The first rotational joint 217D allows the AP slider 214C, and thus the cutting guide 210, to rotate about axis 211A to achieve a slope adjustment of the cutting guide 210, i.e., the adjustment of the orientation of the cut plane in rotation about the medio-lateral axis. To effect this rotation about the axis of the guide rod 216, the first knob 217F is rotated in either direction to cause a rotation of the bracket 217E about axis 211A, which axis is generally parallel to the medio-lateral axis of the patient during surgery. This allows the bracket 217E and the sleeves 217A to rotate, thereby causing the displacement bars 215D to also rotate, to in turn rotate the remainder of the AP slider 214C and the cutting guide 210. The guide adjustment mechanism 214D is therefore able to adjust the cut guide 210 along a flexion-extension orientation relative to a tibia. The guide adjustment mechanism 214D in the depicted embodiment may have a second rotational joint 217H which includes a bracket 217I and a second knob 217J. The second rotational joint 217H allows the AP slider 214C, and thus the cutting guide 210, to rotate about the anterior-posterior axis 211A to adjust the varus-valgus of the cutting guide 210 relative to the tibia. To effect this rotation about the anterior-posterior axis 211B, the second knob 217J is rotated in either direction, which allows the bracket 217E and the sleeves 217A to rotate about the anterior-posterior axis, as axis 211B is generally parallel with the anterior-posterior axis of the tibia, thereby causing the displacement bars 215D to also rotate, to in turn rotate the remainder of the AP slider 214C and the cutting guide 210. According to an embodiment, the second knob 217J has an endless screw portion engaged with a fixed gear on a remainder of the guide adjustment mechanism 214D. Accordingly, a rotation of the knob 217J will result in a fine adjustment of the orientation of the bracket 217I about axis 211B.

Still referring to FIG. 10O, a first sensor bracket 219A for receiving the first inertial sensor 20B may be mounted to the bracket 217E of the guide adjustment mechanism 214D. The first sensor bracket 219A may be displaceable with the guide adjustment mechanism 214D along the axis defined by the guide rod 216, as explained in greater detail below. The second inertial sensor 20B is mounted to a second sensor bracket 219B which is fixedly attached at the second end 216B of the guide rod 216, in proximity to the ankle clamp 216C.

As shown in FIG. 10O, the ankle clamp 216C is located at the second end 216B of the guide rod 216. The ankle clamp 216C has two clamp arms 220A each having a clamp grip 220B at a distal end. The clamp arms 220A and the clamp grips 220B are manipulable to be displaced toward and away from the skin of the patient. Each clamp grip 220B is configured to engage the skin about one of the malleoli of an ankle of the patient. When the clamp grips 220B are mounted to the skin about the malleoli of the patient, a line between the clamp grips 220B represents or approximates a malleolus line, which is a line extending between the malleoli. The clamp grips 220B therefore provide a tibia reference (i.e. the malleolus line), which can be used by the second inertial sensor 20B. The position and orientation of the ankle clamp 216C is adjustable. The ankle clamp 216C is mounted to the second end 216B of the guide rod 216 at an ankle clamp joint 221. The ankle clamp joint 221 includes a mount arm 221A extending between a distal end attached to the second end 216B of the guide rod 216, and a proximal end attached to a pivot bracket 221B. The pivot bracket 221B includes a protrusion 221C which is inserted into an elongated slot 221D to mount the ankle clamp 216C to the second end 216B of the guide rod 216. The ankle clamp 216C is displaceable with respect to the second end 216B of the guide rod 216 with the ankle clamp joint 221. More particularly, a position of the ankle clamp 216C with respect to the second end 216B of the guide rod 216 is adjustable by sliding the protrusion 221C within the slot 221D. The ankle clamp joint 221 also defines a rotational axis RA about which the clamp arms 220A are rotatable relative to the second end 216B of the guide rod 216. The pivot bracket 221B defines the rotational axis RA in the depicted embodiment, and includes a knob 221E to selectively allow pivoting of the clamp arms 220A. The clamp arms 220A are displaceable toward and away from each other, in a direction substantially parallel to the elongated slot 221D, to vary the distance between the clamp arms 220A and accommodate ankles of different sizes.

Still referring to FIG. 100, the length of the guide rod 216 can be adjusted to approximate the length of the tibia 21. In the depicted embodiment, the length of the guide rod 216 can be adjusted telescopically. The guide rod 216 include an inner rod segment 213A nested within an outer rod segment 213B. The mounting bracket 217B of the guide adjustment mechanism 214D is positioned on the inner rod segment 213A, and the second sensor bracket 219B is positioned on the outer rod segment 213B. The inner rod segment 213A is displaceable relative to the outer rod segment 213B to vary the length of the guide rid 216. The displacement of the inner rod segment 213A also displaces the guide adjustment mechanism 214D and the cut guide 210. Navigation tracking is then started by activating the inertial sensors 20A, 20B. The orientation of the guide 210 with respect to the tibia 21 can then be adjusted based on data or feedback from the inertial sensors 20A, 20B, by adjusting the position of the cutting guide 210 using one or more of the AP slider 214C and the guide adjustment mechanism 214D, as described above.

FIG. 10D shows part of the tibia cutting assembly 200 shown in FIG. 100, and like reference numbers therefore denote like features. The cutting guide 310 shown in FIG. 10D has a cut slot 312 which is half the size of the cut slot 212 shown in FIG. 100. The cut slot 312 helps to effect a partial knee surgery, where instead of resecting both condyles and the full tibial plateau, only one condyle and/or one tibial plateau is removed.

Another embodiment is shown in FIGS. 11A to 13. Referring to FIG. 11A, a spike 330 is driven into the entry point for the mechanical axis of the tibia 11. An inertial sensor 20A serving as a tibia reference is mounted onto a sensor bracket 314B, which is then mounted onto the spike 330. In the depicted embodiment, the sensor bracket 314B is slid along the spike 330 in the direction D until it abuts the tibia 11. Once abutted against the tibia 11, the sensor bracket 314B is secured to the tibia 11 with an appropriate fastener. Referring to FIG. 11B, the other inertial sensor 20B is mounted about the ankle A of the patient. The ankle clamp 316C in the depicted embodiment includes a clamp bracket 316F to mount the ankle clamp 316C about the malleoli of the ankle A. The ankle clamp 316C also includes a leg bracket 316G to mount the ankle clamp 316C about the lower leg portion L of the patient to ensure that the ankle clamp 316C is fixed in relation to the ankle A. The other inertial sensor 20B is mounted to a bracket 316H between the clamp and leg brackets 316F, 316G, and is thus instantly fixed in rotation with the tibia 11. With the inertial sensors 20A, 20B secured to the leg, the operator runs through a registration sequence to register the leg and tibia 11 in the reference coordinate system, as shown in FIG. 11C. The operator can verify whether the leg and tibia 11 are properly registered while moving through the sequence by consulting a visual display 340. After the registration sequence has been completed, the ankle clamp 316C can be removed and its inertial sensor 20B used for other purposes, as the inertial sensor 20A on the sensor bracket 314B is calibrated to track the mechanical axis of the tibia 11.

Figure 12A:
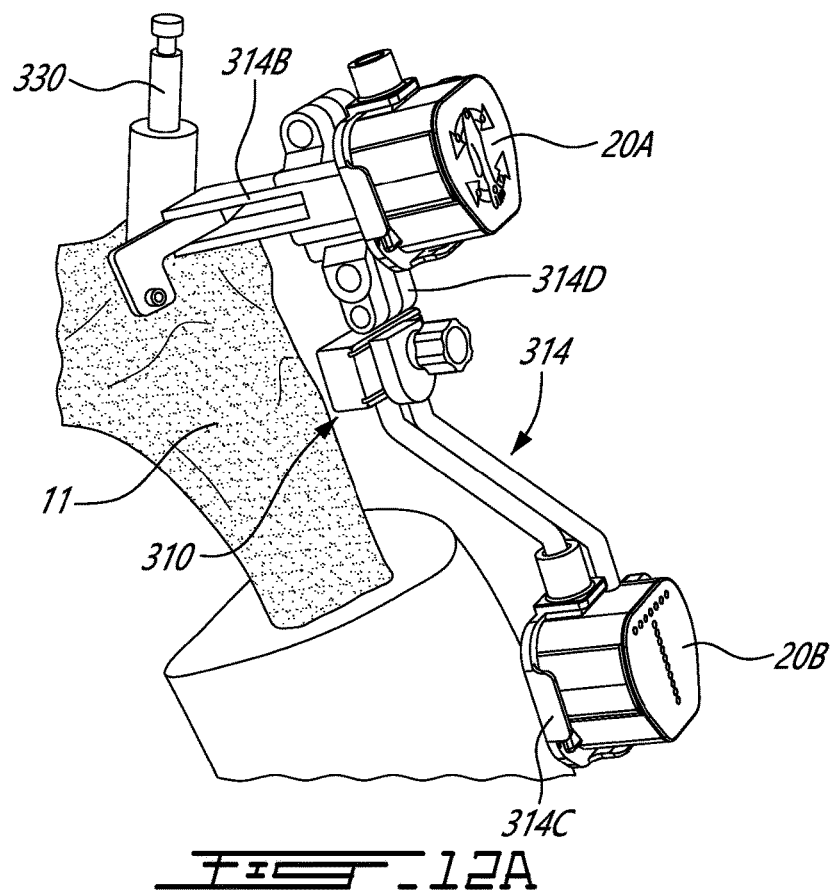

Referring to FIG. 12A, the inertial sensor 20B from the ankle clamp 316C is removed and placed onto the guide holder 314. The guide holder 314 in FIG. 12A is an assembly of different components. One of the components of the guide holder 314 includes a sensor mount 314C for receiving the inertial sensor 20B from the ankle clamp 316C, and another component includes the guide adjustment mechanism 314D which is mounted to the sensor mount 314C. In the embodiment of FIG. 12A, the sensor mount 314C is mounted to, or integral with, the cutting guide 310, such that displacement of the guide adjustment mechanism 314D causes displacement of the sensor mount 314C and the guide 310, in two rotational degrees of freedom, having an axis aligned with the medio-lateral axis for slope adjustment, and with the anterior-posterior axis for varus-valgus adjustment.

The guide adjustment mechanism 314D is then mounted to the sensor bracket 314B, which had been previously secured to the tibia 11. The orientation of the guide 310 with respect to the tibia 11 can then be adjusted with the guide adjustment mechanism 314D based on concurrent data from the inertial sensors 20A, 20B, as described above. Once an appropriate varus/valgus is obtained, the guide 310 can be displaced toward the tibia 11 by sliding the guide adjustment mechanism 314D along the sensor bracket 314B.

Figure 12B:
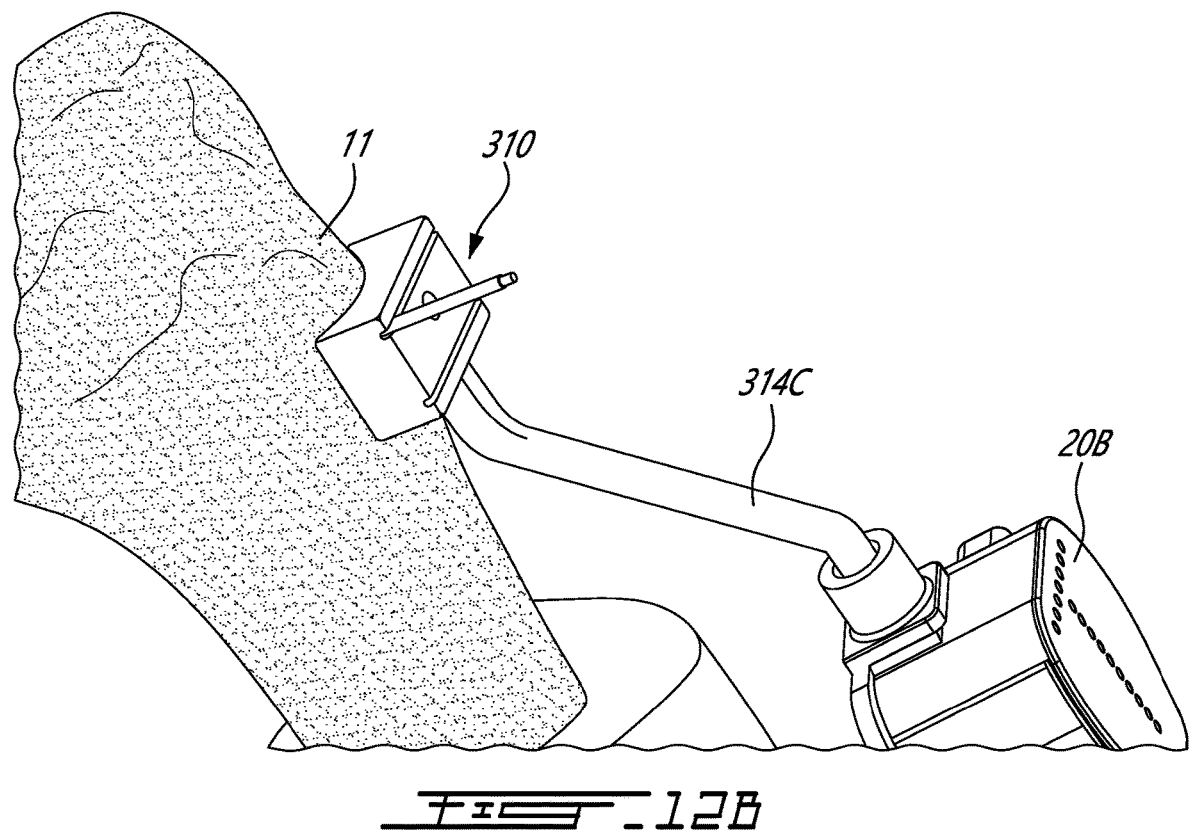

The guide 310 is then secured into place on the tibia 11, for example by pinning the guide 310 to the tibia 11. With the guide 310 secured in position, the guide adjustment mechanism 314D is removed from the sensor mount 314C and from the sensor bracket 314B, the sensor bracket 314B is removed from the tibia 11, and the spike 330 is removed from the tibia 11, leaving only the guide 310 and the attached sensor mount 314C and inertial sensor 20B in place, as shown in FIG. 12B. As shown in FIG. 13, a cut slot body 310A is mounted to the guide 310. The cut slot body 310A houses the cut slot 312 through which the resection operation is effected. In the depicted embodiment, the cut slot body 310A has a mounting leg 310B which is inserted into a mounting hole in the guide 310 to mount the cut slot body 310A to the guide 310. The cut slot body 310A is then secured into place on the tibia 11, for example by pinning the cut slot body 310A to the tibia 11. The surgeon can now effect the resection operation through the cut slot 312.

The above description is meant to be exemplary only, and one skilled in the art will recognize that changes may be made to the embodiments described without departing from the scope of the invention disclosed. For example, the guides described herein may be used with a single inertial sensor unit, mounted to rotate with the cut guide. In such a system, the calibration may assume that the axis of the guide rod is parallel to the mechanical axis of the tibia or in another known orientation. The inertial sensor unit may be calibrated or preset with virtual planning vectors to be operable relative to the mechanical axis. The various joints of the guide may have zero settings for calibration, i.e., the joints may be arranged to be in a known relation relative to one another at given preset arrangements. Other modifications which fall within the scope of the present invention will be apparent to those skilled in the art, in light of a review of this disclosure, and such modifications are intended to fall within the appended claims.

The invention claimed is:

1. A tibia cutting assembly, comprising:
 a tibia cut guide with at least one cut slot, the tibia cut guide being securable to a tibia of a patient;
 a guide rod having a guide holder mountable to the tibia cut guide, the guide rod being displaceable to displace the tibia cut guide and adjust a position thereof with respect to the tibia, and the guide holder cooperating with the tibia cut guide to adjust an orientation of the tibia cut guide, an axis pointer positioned on the guide rod at a first end thereof adjacent to the guide holder, the axis pointer being attachable to the tibia to be indicative of a mechanical axis thereof; and at least one inertial sensor being mountable to the guide holder and being displaceable therewith to determine the orientation of the tibia cut guide;

the guide rod, the axis pointer and part of the guide holder being removable from the tibia cut guide upon the tibia cut guide being secured to the tibia, leaving the tibia cut guide and the at least one inertial sensor secured to the tibia.

2. The tibia cutting assembly of claim 1, wherein the guide holder comprises a guide mount mountable to the tibia cut guide, the guide mount comprising a sensor bracket and the at least one inertial sensor mountable to the sensor bracket, the guide mount and the sensor bracket being securable to the tibia with the tibia cut guide.

3. The tibia cutting assembly of claim 1, wherein the guide holder comprises an anterior/posterior (AP) slider cooperating with the tibia cut guide to displace the tibia cut guide toward and away from the tibia, the AP slider being removable upon the tibia cut guide being secured to the tibia.

4. The tibia cutting assembly of claim 1, wherein the guide holder comprises a guide adjustment mechanism cooperating with the tibia cut guide to adjust the orientation of the tibia cut guide along at least one of a medio-lateral axis and an anterior-posterior axis, the guide adjustment mechanism being removable upon the tibia cut guide being secured to the tibia.

5. The tibia cutting assembly of claim 1, comprising an ankle clamp positioned on the guide rod at a second end thereof and mountable to a skin of the patient about one of a malleolus of an ankle of the patient, the at least one inertial sensor including a first inertial sensor mountable to the guide holder at a first end of the guide rod and a second inertial sensor mountable to the guide rod proximate the second end thereof, the ankle clamp and the second inertial sensor being removable upon the tibia cut guide being secured to the tibia, leaving the tibia cut guide and the first inertial sensor secured to the tibia.

6. The tibia cutting assembly of claim 1, wherein the at least one inertial sensor includes a first inertial sensor being mountable to the guide holder at a first end of the guide rod, and a second inertial sensor being mountable to the guide rod spaced apart from the first inertial sensor, the second inertial sensor being displaceable along the guide rod and configured to be representative of a mechanical axis of the tibia.

7. The tibia cutting assembly of claim 6, wherein the second inertial sensor is removable from the guide rod upon the tibia cut guide being secured to the tibia.

8. A method of securing a tibia cut guide to a tibia of a patient, the method comprising:

mounting the tibia cut guide to a guide rod via a guide holder, and displacing the tibia cut guide with the guide rod or the guide holder;

mounting an inertial sensor to the guide holder;

securing the tibia cut guide to the tibia; and removing the guide rod and part of the guide holder after securing the tibia cut guide to the tibia, leaving the tibia cut guide and the inertial sensor secured to the tibia.

9. The method of claim 8, wherein removing the guide rod and part of the guide holder includes removing the part of the guide holder used to displace the tibia cut guide toward and away from the tibia, or removing the part of the guide holder used to adjust the orientation of the tibia cut guide along at least one of a medio-lateral axis and an anterior-posterior axis.

10. The method of claim 8, wherein securing the tibia cut guide to the tibia includes securing the tibia cut guide and the another part of the guide holder to the tibia.

11. The method of claim 8, wherein mounting the inertial sensor to the guide holder includes mounting a first inertial sensor to the guide holder and mounting a second inertial sensor to the guide rod spaced apart from the first inertial sensor, and wherein removing the guide rod and part of the guide holder includes removing the second inertial sensor after securing the tibia cut guide to the tibia, leaving the tibia cut guide and the first inertial sensor secured to the tibia.

12. A tibia cutting assembly, comprising:

a tibia cut guide with at least one cut slot;

a guide rod having opposed first and second ends, a guide holder being mountable to the guide rod at the first end thereof and to the tibia cut guide, the second end of the guide rod being mountable non-invasively about a skin of the patient, the guide rod being displaceable to displace the tibia cut guide and adjust a position thereof with respect to a tibia of the patient, and the guide holder cooperating with the tibia cut guide to adjust an orientation of the tibia cut guide; and a plurality of inertial sensors, a first sensor being mountable to the guide holder, and a second sensor being mountable to the guide rod spaced apart from the first sensor, the second sensor being displaceable along the guide rod and configured to be representative of a mechanical axis of the tibia.

13. The tibia cutting assembly of claim 12, wherein the second inertial sensor is removable from the guide rod upon the guide rod being aligned with the mechanical axis.

14. The tibia cutting assembly of claim 12, comprising an ankle clamp positioned on the guide rod at the second end thereof and mountable to the skin about malleoli of an ankle of the patient, the second sensor being representative of the mechanical axis of the tibia by using an alignment of the ankle clamp with a malleolus line extending between the malleoli.

15. The tibia cutting assembly of claim 12, wherein the second sensor is mountable to the guide rod at the second end thereof.

16. The tibia cutting assembly of claim 12, wherein the second sensor is mountable to the guide rod between the first and second ends thereof.

17. A method of positioning a tibia cut guide relative to a tibia of a patient, the method comprising:

mounting the tibia cut guide to a guide rod via a guide holder;

mounting a first inertial sensor to the guide holder, and mounting a second inertial sensor to the guide rod spaced apart from the first inertial sensor, mounting the guide rod about a skin of the patient; and displacing the tibia cut guide with the guide rod to align the guide rod with a mechanical axis of the tibia, the second inertial sensor being representative of the mechanical axis of the tibia.

18. The method of claim 17, comprising removing the second inertial sensor after aligning the guide rod with the mechanical axis of the tibia.

19. The method of claim 17, wherein mounting the guide rod about the skin of the patient includes clamping a second end of the guide rod about malleoli of an ankle of the patient, the second inertial sensor being representative of the mechanical axis of the tibia by using a malleolus line extending between the malleoli.

* * * * *